(12) United States Patent
Wong et al.

(10) Patent No.: US 7,718,764 B2
(45) Date of Patent: May 18, 2010

(54) BIOLOGICALLY ACTIVE PEPTIDE VAPEEHPTLLTEAPLNPK DERIVATIVES

(75) Inventors: Wai Ming Wong, Hong Kong (CN); Kong Lam, Shenzhen (CN)

(73) Assignee: CMS Peptides Patent Holding Company Limited, Road Town, Tortola (VG)

( * ) Notice: Subject to any disclaimer, the term of this patent is extended or adjusted under 35 U.S.C. 154(b) by 235 days.

(21) Appl. No.: 11/553,483

(22) PCT Filed: Apr. 25, 2005

(86) PCT No.: PCT/EP2005/004419

§ 371 (c)(1), (2), (4) Date: Oct. 27, 2006

(87) PCT Pub. No.: WO2005/105832

PCT Pub. Date: Nov. 10, 2005

(65) Prior Publication Data

US 2008/0125372 A1    May 29, 2008

Related U.S. Application Data

(60) Provisional application No. 60/566,455, filed on Apr. 28, 2004.

(51) Int. Cl.
  *A61K 38/00* (2006.01)
  *A61K 39/38* (2006.01)

(52) U.S. Cl. .................................... 530/300; 424/184.1

(58) Field of Classification Search ................. 530/300; 424/184.1
  See application file for complete search history.

(56) References Cited

U.S. PATENT DOCUMENTS 6,562,958 B1 * 5/2003 Breton et al. ............. 536/23.7

FOREIGN PATENT DOCUMENTS

| DE | 10133576 A1 | 1/2003 |
|---|---|---|
| WO | 9853322 A1 | 11/1998 |
| WO | 02068601 A2 | 9/2002 |
| WO | 03006492 A2 | 1/2003 |
| WO | WO 03/006492 A2 * | 1/2003 |
| WO | 2004055042 A1 | 7/2004 |

OTHER PUBLICATIONS

Gura (Science, 1997, 278:1041-1042.).*
Molano et al., Peptide Selection by an MHC H-2Kb Class I molecule Devoid of the Central Anchor ("C") Pocket, J. Immun. 1998, 160: 2815-2823.

* cited by examiner

*Primary Examiner*—Sean E Aeder
(74) *Attorney, Agent, or Firm*—Eagle IP Limited; Jacqueline C. Lui

(57) ABSTRACT

Peptides derived from the peptide CMS-010, which has the formula VAPEEHPTLLTEAPLNPK, are disclosed with their use as pharmaceutical compositions. A method is also disclosed for making a pharmaceutical composition comprising providing a peptide derived from CMS-010 and mixing said peptide with a pharmaceutical acceptable carrier.

5 Claims, 5 Drawing Sheets

US 7,718,764 B2

BIOLOGICALLY ACTIVE PEPTIDE VAPEEHPTLLTEAPLNPK DERIVATIVES

CROSS-REFERENCE TO RELATED APPLICATIONS

This application claims the benefit of provisional application Ser. No. 60/566,455 filed on 28 Apr. 2004, under 35 U.S.C. §119(E) (specifically incorporated herein by reference in its entirety)

BACKGROUND OF THE INVENTION

1. Field of the Invention

The present invention is related to short peptides and the use thereof. In particular, the present invention is related to short peptides with biological activities.

2. Description of the Related Art

Peptides are known in the art for treatment of diseases and as pharmaceutical compositions. For example, U.S. Pat. No. 6,191,113 discloses a peptide that has inhibitory activity for the growth of smooth muscle cells and is therefore useful for preventing and treating pathological conditions associated with growth of smooth muscle cells such as arteriosclerosis, restenosis after angioplasty, luminal stenosis after grafting blood vessel and smooth muscle sarcoma. U.S. Pat. No. 6,184,208 discloses another peptide that is found to modulate physiological processes such as weight gain activity of the epithelial growth zone and hair growth. Furthermore, PCT publication no. WO 03/006492 and U.S. patent application Ser. No. 10/237,405 suggested that certain peptides and their pharmaceutical compositions are biologically active and capable of modulating immune responses.

It is therefore an object of the present invention to provide a short peptide or peptides that have biological activity.

SUMMARY OF THE INVENTION

One aspect of the invention relates to peptides derived from the 18 amino acid-containing peptide CMS-010 (VAPEEHPTLLTEAPLNPK) (SEQ ID No. 1) which have been found to contain biological activity, wherein said peptides do not comprise the sequence of the peptide CMS-010. For testing purposes, samples of these peptides were chemically synthesized with L-amino acids. Further aspects of the present invention include an isolated or purified peptide comprising, consisting essentially of or consisting of a sequence selected from SEQ ID No. 2-31, wherein said peptide does not comprise the sequence of the peptide CMS-010 (SEQ ID No. 1). Another aspect relates to substantially pure peptides comprising peptides selected from SEQ ID No. 2-31, wherein said peptides do not comprise the sequence of the peptide CMS-010.

Another aspect of the invention is the administration of a peptide comprising, consisting essentially of or consisting of a sequence selected from SEQ ID No. 2-31, wherein said peptide does not comprise the sequence of the peptide CMS-010, wherein the effects of said administration are selected from the group consisting of the suppression of immune cell transformation, the suppression of NK cell activity, the enhancement of NK cell activity, the suppression of antibody formation in vivo, the suppression of cell proliferation, the suppression of tumor growth, the suppression of nephritis and a decrease in proteinuria. In some embodiments, the suppression of immune cell transformation is the suppression of T-lymphocyte transformation by ConA in vitro. In some embodiments, the suppression of immune cell transformation is the suppression of T-lymphocyte transformation in vivo. In some embodiments, the suppression of cell proliferation is the suppression of the development of sarcoma cells in vivo. In some embodiments, the suppression of nephritis is the suppression of nephritis due to anti-renal epitope antibodies.

Additional aspects of the invention relate to a peptide comprising, consisting essentially of or consisting of a sequence selected from SEQ ID No. 2-31, wherein said peptide does not comprise the sequence of the peptide CMS-010, that consists of L-amino acids. In some embodiments, the peptide comprising, consisting essentially of or consisting of a sequence selected from SEQ ID No. 2-31, wherein said peptide does not comprise the sequence of the peptide CMS-010, is in a substantially pure form.

Another aspect of the invention relates to pharmaceutical compositions comprising a peptide that comprises a sequence selected from SEQ ID No. 2-31, wherein said peptide does not comprise the sequence of the peptide CMS-010. In some embodiments, pharmaceutical compositions comprising a peptide that comprises a sequence selected from SEQ ID No. 2-31, wherein said peptide does not comprise the sequence of the peptide CMS-010, comprise peptides that consist of L-amino acids.

Yet another aspect of the invention are methods of making a pharmaceutical composition comprising providing a peptide that comprises a sequence selected from SEQ ID No. 2-31, wherein said peptide does not comprise the sequence of the peptide CMS-010, and mixing the peptide with a pharmaceutically acceptable carrier.

Still another aspect of the invention are methods of reducing the effects of a human disease comprising administering a pharmaceutically effective dose of a peptide that comprises a sequence selected from SEQ ID No. 2-31, wherein said peptide does not comprise the sequence of the peptide CMS-010. In some embodiments, said human is suffering from a cell proliferative and/or an immunological disorder. In some embodiments, the cell proliferative disorder is a cancer, a sarcoma and/or a tumor.

An additional aspect of the invention is a method of modulating the immune system of an individual comprising administering a pharmaceutically effective dose of a peptide that comprises a sequence selected from SEQ ID No. 2-31, wherein said peptide does not comprise the sequence of the peptide CMS-010.

Another aspect of the invention is the use of a peptide that comprises a sequence selected from SEQ ID No. 2-31 as a pharmaceutical compound, wherein said peptide does not comprise the sequence of the peptide CMS-010. In some embodiments, the peptide is used for treating a disease state in the form of a cell proliferative disorder and/or an immunological disorder. In some embodiments, the cell proliferative disorder being treated is a sarcoma.

Yet another aspect of the invention is the use of a peptide that comprises a sequence selected from SEQ ID No. 2-31 as an immune system modulator, wherein said peptide does not comprise the sequence of the peptide CMS-010. In some embodiments, the modulation of the immune system is the enhancement or suppression of NK cell activity.

An additional aspect of the invention is the use of a peptide that comprises a sequence selected from SEQ ID No. 2-31 as a nutritional supplement, wherein said peptide does not comprise the sequence of the peptide CMS-010.

Another aspect of the invention is a molecule comprising an enhanced derivative of a peptide that comprises a sequence selected from SEQ ID No. 2-31, comprising an enhancement molecule operably linked to said peptide, wherein the enhancement molecule enhances the therapeutic effectiveness of said peptide and said peptide does not comprise the sequence of the peptide CMS-010.

BRIEF DESCRIPTION OF THE DRAWINGS

Each of the five figures demonstrates exemplary chemical reactions for linking peptides to steroid molecules.

DETAILED DESCRIPTION OF THE PREFERRED EMBODIMENT

I. Introduction

Figure 1:
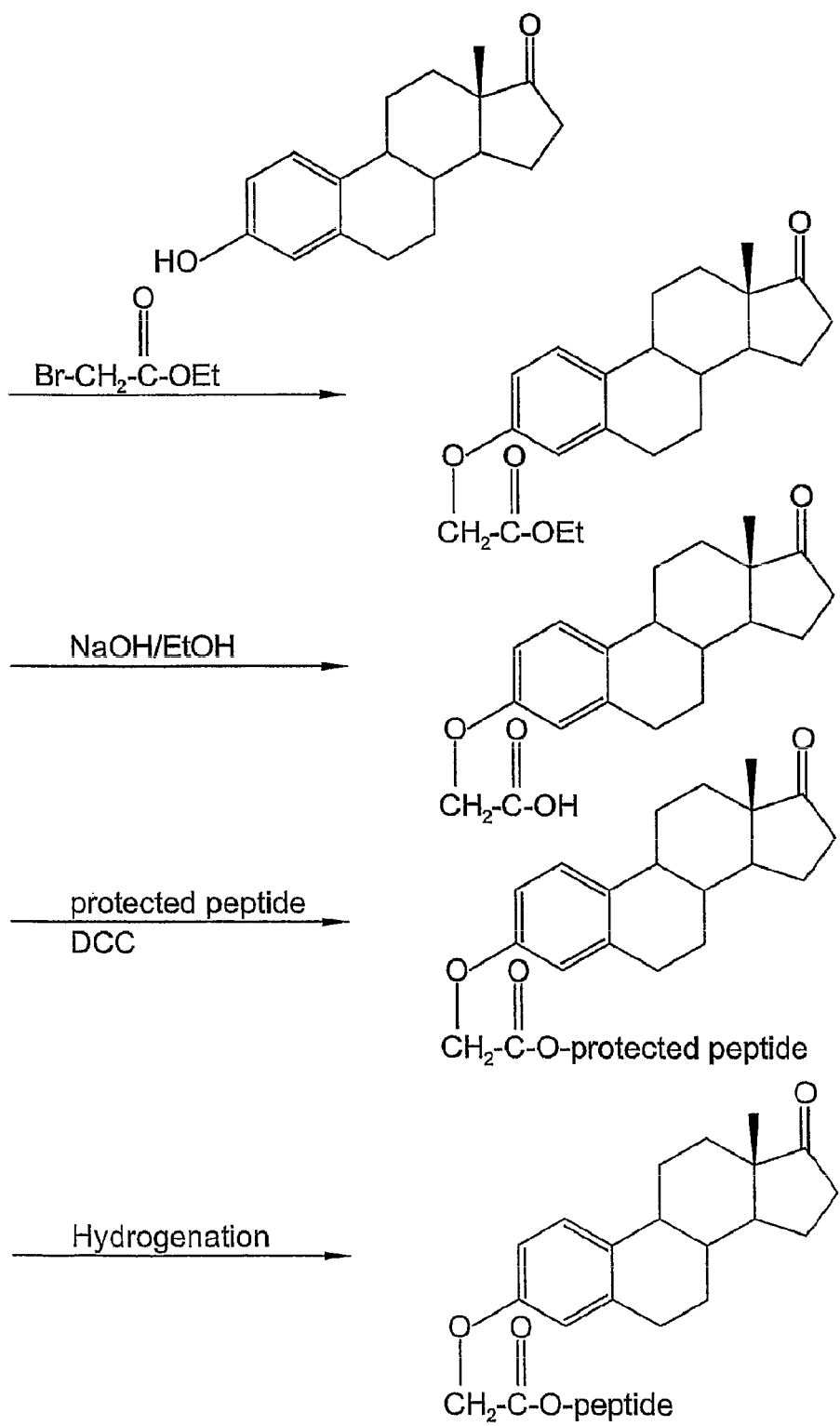
FIG. 1 shows a series of chemical reactions for linking a peptide to an estrone molecule with a covalent bond.

The peptide CMS-010 (SEQ ID No. 1), having the sequence VAPEEHPTLLTEAPLNPK, was discovered to have biological immuno-regulatory activity (U.S. patent application Ser. No. 10/178,684) and has therapeutic potential for human use. The present invention relates to fragments and derivatives of CMS-010 that have biological activity. In particular embodiments, the invention includes the fragments and derivatives whose sequences are given as SEQ ID No. 2-31. In some embodiments, the fragments may have substitutions and/or additional molecular groups, or may be functional derivatives of VAPEEHPTLLTEAPLNPK (CMS-010). Uses of the CMS-010 fragments and derivatives include the regulation of cells and tissues. CMS-010 fragments and derivatives can be incorporated in pharmaceutical preparations and nutritional supplements.

It is understood that it may be possible to add additional amino acids to the amino or carboxyl termini of a peptide that comprises, consists essentially of or consists of a sequence selected from SEQ ID No. 2-31, wherein said peptide does not comprise the sequence of CMS-010, and functional derivatives thereof as another method of practicing the present invention. In such embodiments, a peptide that comprises, consists essentially of or consists of a sequence selected from SEQ ID No. 2-31, wherein said peptide does not comprise the sequence of CMS-010, and functional derivatives thereof maintains one or more of the therapeutic or functional properties described herein. For example, in some embodiments, one or two amino acids may be added to a disclosed peptide without affecting its biological function. In some embodiments, smaller molecules containing some portion of VAPEEHPTLLTEAPLNPK (CMS-010) comprise a single stretch of sequence derived from VAPEEHPTLL-TEAPLNPK (CMS-010). In other embodiments, smaller molecules containing some portion of VAPEEHPTLLTEA-PLNPK (CMS-010) comprise two or more stretches of sequence derived from separate, non-contiguous portions of VAPEEHPTLLTEAPLNPK (CMS-010). For example, in some embodiments, smaller molecules containing some portion of VAPEEHPTLLTEAPLNPK (CMS-010) comprise sequence found near the N-terminus of VAPEEHPTLLTEA-PLNPK (CMS-010) as well as sequence found near the C-terminus of VAPEEHPTLLTEAPLNPK (CMS-010), without any intervening sequence found between the two sequences in VAPEEHPTLLTEAPLNPK (CMS-010). In further embodiments, it may also be possible to add three or four amino acids and still maintain the function of a peptide selected from the group consisting of fragments of CMS-010 (VAPEEHPTLLTEAPLNPK) (wherein said fragments do not comprise the sequence of CMS-010) and functional derivatives thereof. These are all referred to as variants of the same peptide. Furthermore, derivatives of a peptide, such as conservative replacement of one amino acid for another within the same functional class, may be used to practice another aspect of the present invention. For example, peptides having non-polar or hydrophobic side chains may be possible to substitute one side group for another without reducing biological activity. In some embodiments, a peptide fragment of CMS-010 can have one, two or more amino acids eliminated from the sequence while still retaining the activity of the original peptide fragment. For example, a peptide fragment of CMS-010 that is ten amino acids in length is resynthesized without the $5^{th}$ amino acid from the N-terminal end in the sequence. Thus the resulting variant is only 9 amino acids in length, has the $4^{th}$ amino acid from the N-terminal end covalent linked to the $6^{th}$ amino acid from the N-terminal end in the original sequence and yet still has the same activity as the original peptide fragment with ten amino acids. In some embodiments where two or more amino acids are eliminated from the sequence of a peptide fragment of CMS-010, the amino acids that are eliminated are adjacent to one another in the original peptide fragment sequence. In other embodiments where two or more amino acids are eliminated from the sequence of a peptide fragment of CMS-010, the amino acids are not adjacent to one another in the original sequence, but rather are separated from one another in the original sequence by amino acids that remain in the shortened, variant peptide. In additional embodiments where three or more amino acids are eliminated from a peptide fragment of CMS-010, some amino acids eliminated from the original peptide fragment sequence are adjacent to one another while one or more amino acids eliminated from the original sequence are not adjacent to any other amino acids from the original sequence that were eliminated. In additional embodiments of the invention, a linker/spacer sequence may be inserted into the peptide to form variants, but the variants still retain their active moiety as the original peptide used in this study. These are also considered variants of the peptides. A peptide analogue as used herein, includes peptides that have amino acid molecules that mimic the structure of the natural amino acid, e.g. an analog with a different backbone structure, or D-amino acid substitution. As a further example, although the amino acids used for synthesizing the peptides are in their L optical isomeric form, peptides with one or more of the amino acids in the sequence substituted with the D-form may have similar biological activities. The term "functional derivative" as used in the claims is meant to include fragments, variants, analogues or chemical derivatives of the peptide.

"Substantially pure peptide" refers to peptides that are at least 10% w/w in purity, more preferably 20%, even more preferably 40% and much more preferably 60% and far more preferably larger than 90% pure. In the most preferred embodiment, the purity is larger than 99%. The substantially pure peptide can be used to prepare pharmaceutical and nutritional formulations that may be complex mixtures as described below.

"Modulation" refers to an effect on cells mediated by administration or exposure to peptides of the invention, wherein administration or exposure of peptides to cells causes changes in the activities of the cells. The changes may be to enhance or to suppress the activity of a cell. The enhancement or suppression of the activity of a cell may be the enhancement or suppression of the rate of cell division and replication, the enhancement or suppression of the reaction of the cell to other elements, and/or the enhancement or suppression of the rate of production and/or secretion of proteins or compounds from the cell.

"Cell proliferation" refers to an increase in the number of cells present and may be due to transformation or immortalization of a cell. Cell proliferation disorders include, but are not limited to, cancers, benign growths, tumors and sarcomas and may encompass any number of cells. "Immunological disorders" refers to a malfunction or deleterious function of an immune cell or other part of the immune system. Such disorders may be caused by the suppression of activity of a cell or molecule or the enhancement of the activity of a cell or molecule.

The use of a peptide that comprises, consists essentially of or consists of a sequence selected from SEQ ID No. 2-31, wherein said peptide does not comprise the sequence of CMS-010, and functional derivatives thereof, in pharmaceutical formulations may be employed as possible treatment for immunological disorders or disease. The formulations may have a peptide that comprises, consists essentially of or consists of a sequence selected from SEQ ID No. 2-31, wherein said peptide does not comprise the sequence of CMS-010, and functional derivatives thereof, mixed with other active or inactive constituents, including other peptides, e.g. two to several (e.g. 3-5) peptides may be added to the same formulation with or without other ingredients. Alternatively, a peptide that comprises, consists essentially of or consists of a sequence selected from SEQ ID No. 2-31, wherein said peptide does not comprise the sequence of CMS-010, and functional derivatives thereof, may be used to prepare the formulation together with peptides not listed here. They can be administered in the form of intravenous, intramuscular, intracutaneous, subcutaneous or intradermal. The mode of administration may also be intra-arterial injection that leads directly to the organ of problem. Other modes of administration are transdermal, inhalation as powder or spray, and other forms of delivery known by one in the art. The formulation may also be orally taken, and may contain carriers that can be used to prevent gastric digestion of the peptide after oral intake or any other carriers known in the art (a carrier for transdermal delivery, such as liposomes, for example).

As used herein, the term "hybrid peptide" is used to refer to peptides that contain additional peptides inserted into the original biologically active peptide having the sequence specified above or its functional derivatives, but still retain substantially similar activity. The additional peptides include leader peptides that contain, for example, an amino acid sequence that is recognized by one or more prokaryotic or eukaryotic cell as a signal for secretion of the hybrid protein into the exterior or the cell. The secretion may be a direct secretion, or indirectly through secretory vesicles.

As used herein, the terminology "consisting essentially of" refers to a peptide or polypeptide that comprises, consists essentially of or consists of a sequence selected from SEQ ID No. 2-31, wherein said peptide does not comprise the sequence of CMS-010, and functional derivatives thereof, along with additional amino acids at the carboxyl and/or amino terminal ends and which maintains one or more of the activities of said peptides provided herein. Thus, as a non-limiting example, where the activity of a peptide that comprises, consists essentially of or consists of a sequence selected from SEQ ID No. 2-31, wherein said peptide does not comprise the sequence of CMS-010, and functional derivatives thereof, is to treat and/or prevent cell proliferative or immunological disorders or diseases, a peptide or polypeptide "consisting essentially of" the peptide that comprises, consists essentially of or consists of a sequence selected from SEQ ID No. 2-31, wherein said peptide does not comprise the sequence of CMS-010, and functional derivatives thereof, will possess the activity of treating and/or preventing disorders or diseases as provided herein with respect to that peptide and will not possess any characteristics in and of itself (i.e. before modification by attachment to one or more biologically active molecules) which materially reduces the ability of the peptide or polypeptide to treat or prevent cell proliferative or immunological disorders or which constitutes a material change to the basic and novel characteristics of the peptide as a treatment for and/or preventor of the above disorder or disease. Thus, in the foregoing example, a full length naturally occurring polypeptide which has a primary activity other than treating and/or preventing cell proliferative or immunological disorders and which comprises, consists essentially of or consists of a sequence selected from SEQ ID No. 2-31 and functional derivatives thereof somewhere therein (but does not comprise the sequence of CMS-010) would not constitute a peptide or polypeptide "consisting essentially of" the peptide that comprises, consists essentially of or consists of a sequence selected from SEQ ID No. 2-31 and functional derivatives thereof whose sequence is contained in the full length naturally occurring polypeptide. Likewise, in the foregoing example, a genetically engineered peptide or polypeptide which has a primary activity other than treating or preventing cell proliferative or immunological disorders but includes the amino acid sequence of a peptide that comprises, consists essentially of or consists of a sequence selected from SEQ ID No. 2-31 (but does not comprise the sequence of CMS-010) and functional derivatives thereof somewhere therein would not constitute a peptide or polypeptide "consisting essentially of" the peptide that comprises, consists essentially of or consists of a sequence selected from SEQ ID No. 2-31 (but does not comprise the sequence of CMS-010) and functional derivatives thereof whose sequence is contained in the genetically engineered peptide or polypeptide.

Those skilled in the art can readily determine whether a peptide or polypeptide consists essentially of a peptide that comprises, consists essentially of or consists of a sequence selected from SEQ ID No. 2-31, wherein said peptide does not comprise the sequence of CMS-010, and functional derivatives thereof under the foregoing definitions by measuring the activity of the peptide or polypeptide using the assays for treating or preventing cell proliferative or immunological disorders, which are provided herein with respect to fragments and derivatives of the VAPEEHPTLLTEAPLNPK (CMS-010) peptide.

In the preferred embodiment, the terminology "consisting essentially of" may also refer to peptides or polypeptides which have less than 5 amino acid residues in addition to a peptide that comprises, consists essentially of or consists of a sequence selected from SEQ ID No. 2-31, wherein said peptide does not comprise the sequence of CMS-010, and functional derivatives thereof. In a more preferred embodiment, the same terminology refers to peptides with 2 amino acid residues in addition to a peptide that comprises, consists essentially of or consists of a sequence selected from SEQ ID No. 2-31, wherein said peptide does not comprise the sequence of CMS-010, and functional derivatives thereof. In an even more preferred embodiment, the same terminology refers to a peptide with one amino acid residue in addition to a peptide that comprises, consists essentially of or consists of a sequence selected from SEQ ID No. 2-31, wherein said peptide does not comprise the sequence of CMS-010, and functional derivatives thereof.

The pharmaceutical formulation may include any of the known pharmaceutical carriers. Examples of suitable carriers include any of the standard pharmaceutically accepted carrier known to those skilled in the art. These include but are not limited to, physiological saline solution, water, emulsions including oil and water mixtures or triglyceride emulsions, and other types of agents, fillers, coated tablets and capsules. The appropriate carrier may be selected based on the mode of administration of the pharmaceutical composition.

A peptide selected from the group that comprises, consists essentially of or consists of a sequence selected from SEQ ID No. 2-31, wherein said peptide does not comprise the sequence of CMS-010, and functional derivatives thereof, may be administered via intravenous injection, intramuscular injection, intraperitoneal injection, subcutaneous injection, and subcutaneous implantation. The peptide may also be administered in any form of oral administration like tablet, capsule, suspension, solution etc, in the usual form without modification or in slow release form, or with or without gastro-enteric protection. The peptide may further be applied in any form of topic application like ointment, cream, gel, etc., with or without transdermal facilitating device. The peptide may also be interpreted into its genetic sequence and cloned into an expression system, on its own or in combination with other peptide sequences, to generate a resulting peptide molecule to make use of the activity of the peptide as described herein.

The dose of each peptide may be 1 ng-10 g per kg body weight. A preferred dose is 10 ng-10 mg per kg, and more preferably 1 µg-1 mg per kg for an injection mode of administration. However, the effective dose can be as low as 1 ng per kg body weight, since one or more of the peptides may operate through receptors that will induce a cascade of normal physiological response. Alternatively, one or more of the peptides can just be an initiator for a whole cascade of reaction. For an oral intake, the amount may be 1 ng-10 g per day per kg body weight, more preferably 0.1 µg-1 g per day per kg body weight and even more preferably 1 µg-10 mg per day.

II. Gene Therapy and Method of Treatment

Gene therapy based on the above peptide sequences is performed by designing a nucleic acid sequence that codes for one of these peptides. The nucleic acid may be synthesized chemically and operably ligated to a promoter, and cloned into an expression vector. The expression vector is then administered into the human body as the form of gene therapy for expression in the human cell. The term "genetic vectors" as used herein includes these expression vectors. Vectors that can be used for gene therapy includes adeno-associated virus (Mizuno, M. et al. (1998). Jpn J Cancer Res 89, 76-80), LNSX vectors (Miller, A. D. et al. (1993) Methods Enzymol 217, 581-599) and lentivirus (Goldman, M. J. et al. (1997) Hum Gene Ther 8, 2261-2268).

Other vehicles for peptide delivery include expression vectors encoding the desired peptide that can be transferred into an organism which can replicate in the host organism to which it is desired to administer the peptide without significant detrimental effects on the health of the host organism. For example, the expression vectors may be transferred into an organism that is not pathogenic to the host organism to which it is desired to administer the peptide. In some embodiments the expression vector produces the desired peptide in a bacterial or fungal organism that does not have significant detrimental effects on the health of the host organism to which the peptide is to be administered. For example, the expression vector encoding the desired peptide may be an expression vector that produces the desired peptide in an organism such as lactic acid bacteria, E. Coli, or yeast. In one embodiment, the expression vector produces the desired peptide in a microbe normally found in the mammalian gut or a microbe tolerated by the mammalian digestive tract. Some of the microbial species in which the desired peptide can be expressed include, but are not limited to, Lactobacillus species, such as L. acidophilus, L. amylovorus, L. casei, L. crispatus, L. gallinarum, L. gasseri, L. johnsonii, L. paracasei, L. plantarum, L. reuteri, L. rhamnosus or others; Bifidobacterium species, such as B. adolescentis, B. animalus, B. bifidum, B. breve, B. infantis, B. lactis, B. longum or others; Enterococcus faecalis or Ent. facium; Sporolactobacillus inulinus; Bacillus subtilis or Bacillus cereus; Escherichia coli; Propionibacterium freudenreichii; or Saccharomyces cerevisiae or Saccharomyces boulardii.

Nucleic acid sequences that encode any of the peptides of the present invention, chemically synthesized or produced by other means, including but not limited to the reverse transcription of mRNA to produce cDNA molecules, are incorporated into expression vectors for gene transfer into the desired organisms by methods of genetic engineering familiar to those of skill in the art. The expression vectors may be DNA vectors or RNA vectors. For example, the expression vectors may be based on plasmid or viral genetic elements. The expression vectors may be vectors that replicate extra-chromosomally or vectors that integrate into the chromosome.

The expression vectors comprise a promoter operably linked to a nucleic acid encoding a peptide of the present invention. The promoter may be a regulatable promoter, such as an inducible promoter, or a constitutive promoter. In some embodiments, the promoter may be selected to provide a desired level of peptide expression. In addition, if desired, the expression vectors may comprise other sequences to promote the production, presentation and/or secretion of peptides. In some embodiments a nucleic acid encoding a peptide of the present invention is operably linked to a nucleic acid sequence which directs the secretion of the peptide. For example, the nucleic acid encoding the peptide of the present invention may be operably linked to a nucleic acid encoding a signal peptide.

In some embodiments, the expression vectors which are engineered to encode the peptides of the present invention may be expression vectors which are adapted for expressing the peptide of the present invention in a bacterial species that makes up the normal gut flora of mammals, such as Lactobacillus species and Bacillus subtilis. Examples of such expression vectors can be found in U.S. Pat. No. 6,100,388, to Casas, and No. 5,728,571, to Bellini, respectively. These documents are hereby expressly incorporated by reference in their entireties. It will be appreciated that any expression vector which facilitates the expression of a peptide of the present invention in an organism that is not detrimental to the health of the host organism to which the peptide is to be administered may be used.

In some embodiments, the expression vectors which are engineered to encode the peptides of the present invention may be expression vectors which are adapted for expressing the peptide of the present invention in a yeast species that is well tolerated by the mammalian gut, such as Saccharomyces cerevisiae; or, preferably, Saccharomyces boulardii, which can colonize the human gut and is used to treat certain forms of diarrhea. Yeast expression vectors can be used that constitutively express heterologous proteins and peptides, are highly stable, thus are well transmitted to progeny cells during mitosis and meiosis and may comprise coding sequence for a signal peptide or peptides that direct high levels of recombinant protein secretion. An example of such a yeast vector is given in U.S. Pat. No. 6,391,585, to Jang et al., which is hereby expressly incorporated by reference in its entirety.

The expression vectors encoding the peptides of the present invention may be introduced into the organism in which it is intended to express the peptides through techniques known in the art. These techniques include traditional methods of transforming bacteria, yeast, or other microbes, through the use of chemically competent bacterial cells, electroporation or lithium acetate transformation (for yeast), for example, as well as recent advances in the transformation of bacterial species recalcitrant to these procedures. In some embodiments, the expression vectors are introduced into lactic acid bacteria known to be recalcitrant to transformation using the method disclosed by Leer et al. (WO 95/35389), the disclosure of which is incorporated herein by reference in its entirety. The introduced sequences may be incorporated into microbial chromosomal DNA or may remain as extrachromosomal DNA elements.

This genetically engineered microbe containing the expression vector can then be inoculated into the alimentary canal, vagina, trachea etc. to achieve sustained immunotherapy. In some embodiments, the organisms expressing the peptides of the present invention are ingested in an inactive form or, preferably, in live form. In the gut these microorganisms produce said peptides, release them into the lumen by secretion or by lysis of the microorganism or otherwise present the peptides to the host, whereby the peptides produce their intended effect upon the host organism. In other embodiments, peptides are presented to the host at the mucous membrane of the nasal passages, vagina or the small intestine.

Another method of the treatment is the use of liposomes as a means for delivering the specific nucleic acid to the cells in the human body. The nucleic acid (such as an expression vector containing a nucleic sequence that encodes a peptide that comprises, consists essentially of or consists of a sequence selected from SEQ ID No. 2-31, wherein said peptide does not comprise the sequence of CMS-010, and functional derivatives thereof) is delivered in an environment that encourages cellular uptake and chromosomal incorporation as described in Gao, X. and Huang, L. (1995) Gene Ther 2, 710-722 and U.S. Pat. No. 6,207,456. Alternatively, the peptide itself can be encapsulated in the liposome and delivered directly, using a method described in U.S. Pat. No. 6,245,427. All the scientific publications and patents indicated above are incorporated herein by reference in their entireties.

The nucleic acid sequences useful for the above-mentioned gene therapy and method of treatment include sequences that code for these peptides and functional derivatives thereof. Any one of the numerous nucleic acid sequences may be used to code for these peptides and their derivatives based on the degenerate codon system.

The following references are incorporated herein by reference in their entireties.
1. Principles of Pre-clinical Research of New Drugs, People's Republic of China. 1993, 7:134-135 Shuyun Xu, Rulian Bian, Xiu Chen. Methodology of pharmacological experiment. People's Health Publishing House. 1991, 1221-1234
2. Principle of new drug research in pre-clinic issued by Ministry of Health, People's Republic of China. 1993, 7:140
3. Jinsheng He, Ruizhu Li, Tingyi Zong. The study on MTT reduction method of testing NK cell activity. China Immunology Journal. 1996, 1(6): 356-358
4. Qian Wang. Modern medical experiment method. People's Health Publishing House. 1998, 482-483
5. Principle of new drug research in pre-clinic issued by Ministry of Health, People's Republic of China. 1993, 7: 141
6. Principle of new drug research in pre-clinic issued by Ministry of Health, People's Republic of China. 1993, 7: 132-133
7. Principle of new drug research in pre-clinic issued by Ministry of Health, People's Republic of China. 1993, 7: 128-129
8. Yuanpei Zhang, Huaide Su. Pharmalogical experiment (second edition). People's Health Publishing House. 1998, 137-138
9. Jiatai Li, clinical pharmacology (second edition). People's Health Publishing House. 1998, 1338-1339.

III. Peptide Conjugations to and Formulations with Peptides That Comprise, Consist Essentially of or Consist of SEQ ID No. 2-31 (Wherein Said Fragments do not Comprise the Sequence of CMS-010) and Functional Derivatives Thereof The biologically active peptides of the present invention may be conjugated to other biologically effective or useful molecules to provide an additional effect or use or to enhance their therapeutic effectiveness. Many potential conjugating molecules, their biological effects and the methods for conjugation of the molecules to peptides are known in the art. For other candidate conjugation partners, chemical reactions for conjugating the instant peptides thereto can be deduced by one skilled in the art without undue experimentation. Effective molecules are described below. Specific examples of how various peptides according to the present invention may be conjugated to their effective molecules and the biological properties of the resulting conjugation product are described. It is understood that other peptides of the instant invention may also be conjugated in similar reactions.

The peptide fragments that comprise, consist essentially of or consist of a sequence selected from SEQ ID No. 2-31, wherein said peptide fragments do not comprise the sequence of CMS-010, and functional derivatives thereof, can have distinct therapeutic effects on particular cells or tissue types. One important objective of conjugating molecules to peptide drugs is the targeting of the peptide to a particular location or compartment within the body of an individual being treated. In this way, the peptide drug and its effects can be concentrated at the location of the cell or tissue type on which it has the intended therapeutic effect. This can augment the effect that a similar molar amount of the free, unconjugated peptide would have. Conversely, the dosage of a conjugated peptide drug that is targeted to its therapeutic active site can be significantly lower than the dosage required to get the same therapeutic effect from the free, unconjugated form of the drug.

Another beneficial effect of targeting a peptide drug to the site where its activity is most desired is the reduction of unwanted side effects. A peptide drug that is administered in order to effect a change in a particular cell or tissue type can also act in other locations within an individual, sometimes with detrimental results. By targeting the peptide to the desired location of activity via conjugation to a targeting molecule, the concentration of peptide elsewhere in the individual and the subsequent side effects can be reduced.

Peptides that comprise, consist essentially of or consist of a sequence selected from SEQ ID No. 2-31, wherein said peptides do not comprise the sequence of CMS-010, and functional derivatives thereof, can be conjugated to a variety of molecules for targeting to different locations throughout the body of an individual. Any of the conjugation technologies described below for targeting a peptide to a desired location, as well as other conjugation technologies familiar to those skilled in the art, may be employed with any of the peptides of the present invention. For example, the selective delivery of an anti-hepatitis B drug to liver cells has been demonstrated (Fiume et al., Ital J Gastroenterol Hepatol, 29 (3):275, 1997, which is incorporated herein by reference in its entirety). In this study, researchers conjugated adenine arabinoside monophosphate (ara-AMP), a phosphorylated nucleoside analogue active against hepatitis B virus, to lactosaminated human albumin, a galactosyl-terminating macromolecule. Hepatocytes express a receptor protein that interacts with terminal galactosyl residues with high affinity. Through binding to this receptor, the conjugated drug will be selectively taken up by hepatocytes. After absorption, the conjugated drug is delivered to lysosomes, where the bond between the two components of the conjugated drug is cleaved, releasing ara-AMP in its active form. In the study cited above, the conjugated drug was as effective as free ara-AMP in treating patients with chronic hepatitis B infections, but did not cause the clinical side effects, such as neurotoxicity, that the administration of free ara-AMP causes. Such an approach can be used with any of the peptides of the present invention.

In a related study to the one above, by the same research team (Di Stefano et al., Biochem. Pharmacol., 61 (4):459, 2001), an anti-cancer chemotherapeutic agent, 5-fluoro 2-deoxyuridine (FUdR), was conjugated to lactosaminated poly-L-lysine in order to target the compound to the liver and treat liver micrometastases. The drug is selectively taken up by liver cells, which cleave the bond between FUdR and the targeting molecule. A portion of the free FUdR will then exit the liver cells and a localized therapeutic concentration of the anti-cancer agent is created. This concentration is sufficient for pharmacological activity on the metastatic cells that have infiltrated the liver. Because the drug is selectively concentrated in the liver, the dosage of the conjugated drug can be significantly less than the smallest pharmacologically active dosage of the free, unconjugated compound. This strategy can be utilized with any of the peptides of the present invention. For instance, conjugation of lactosaminated poly-L-lysine to a peptide that comprises, consists essentially of or consists of a sequence selected from SEQ ID No. 2-31 (wherein said peptide does not comprise the sequence of CMS-010) and functional derivatives thereof could significantly reduce the dosage necessary to treat or prevent a cell proliferative disorder involving liver tissues.

The targeting of compounds to particular tissues or cell types within the body has been achieved for a number of different tissues or cell types. For example, tumor cells often express abnormally high levels of peptide hormone receptors on their surfaces, such as bombesin, lutenizing hormone-releasing hormone, and somatostatin. In one study, the anticancer compound paclitaxel (taxol) has been selectively targeted to hormone-secreting tumor cells that express somatostatin receptors at a high density by conjugating the drug with octreotide, an analog of somatostatin. The ostreotide-conjugated taxol was just as effective as free taxol but with reduced toxicity to normal cells (Huang et al., Chem. Biol., 7 (7):453, 2000). Using the techniques of Huang et al. to conjugate peptides of the present invention to analogs of peptide hormone receptor agonists would create a treatment specifically targeting cells expressing high levels of that particular peptide hormone receptor. This approach can be adapted to target cells overexpressing any number of peptide hormone receptors. In another example of targeting a drug to a specific tissue type, poly(L-aspartic acid) was used as a carrier molecule to target drug delivery to colon cells specifically (Leopold et al., J. Pharmacokinet. Biopharm., 23 (4): 397, 1995).

Beyond the specific targeting of a peptide drug to a particular cell or tissue type, conjugation of peptides comprising, consisting essentially of, or consisting sequences selected from SEQ ID No. 2-31 (wherein said sequences do not comprise the sequence of CMS-010) and functional derivatives thereof to carrier molecules can provide other ways to enhance the delivery of peptide drugs, thereby augmenting or otherwise improving their therapeutic effects. Any of the conjugation technologies described below may be used with any of the peptides of the present invention, as with other technologies familiar to those skilled in the art. The effectiveness of any drug will be hampered if the compound cannot be delivered to its target efficiently. A drug must be transported, actively or otherwise, to the site of its activity without substantial loss of activity due to metabolic processing or degradation. Peptide drugs are subject to the activity of peptidases and, as highly charged molecules, can be refractory to transport across lipid cell membranes and endothelial cell membranes, such as the blood-brain barrier. Conjugation to other molecules provides a way to protect peptides from degradation and to enhance the absorption of peptide drugs into cells or anatomical compartments that would normally exclude the compounds.

By allowing peptides access to locations within the body from which they would normally be excluded, conjugation techniques can open up new routes for administration of the drug. In Patel et al., Bioconjugate Chem., 8 (3):434, 1997, the chemistry of which is detailed in Example 5 below and which is incorporated herein by reference in its entirety, researchers conjugated a peptide drug known to be a potent analgesic, the heptapeptide deltorphin, to an organic molecule that was specifically designed to allow the peptide to cross the blood-brain barrier. This allows the drug to be administered intravenously instead of by intracerebro ventricular injection.

The carrier molecule in Patel et al. was designed to specifically target those endothelial cells that comprise the blood-brain barrier in addition to allowing the peptide to get across the barrier. Endothelial cell membranes throughout the body, including the blood brain barrier, are heterogeneous with regards to the sequence specificity and concentration of membrane-bound endopeptidases that are displayed on their surfaces. The design of the molecule exploits this characteristic to enable targeting of the carrier molecule and its cargo. The molecule contains three fatty acid chains whose free ends are capped with the dipeptide Arg-Pro, which will interact preferentially with the endopeptidases of the blood brain barrier. The transportation of the charged peptide drug molecule is then enabled by the lipophilic fatty acid chains. Thus the dipeptide-capped triglyceride molecule permits both the targeting and the transport across the blood brain barrier.

Conjugation methods can also enhance the kinetics of a peptide drug's activity. Any of the conjugation technologies described below for enhancing the kinetics of a peptide's activity as well as other conjugation technologies familiar to those skilled in the art may be employed with a peptide that comprises, consists essentially of or consists of a sequence selected from SEQ ID No. 2-31 (wherein said peptide does not comprise the sequence of CMS-010) and functional derivatives thereof. Patel et al. found that the conjugated form of the analgesic peptide was not only able to enter the brain from the bloodstream, but had sustained action in comparison to the free peptide as well. The intravenously administered drug took longer to have a therapeutic effect, but the effect lasted longer and decreased more slowly than the effect of the free peptide injected intracranially. The researchers found that the conjugated peptide molecule is remarkably stable in serum, yet had no effect when injected intracerebro ventricularly, indicating that the carrier molecule is likely degraded and removed during its transport from the bloodstream to the brain. They suspect that the time required to transport the conjugate and degrade the carrier molecule is the cause of the altered kinetics. Regardless of the mechanics of the delay, in a clinical setting, the intravenous stability of the conjugated peptide molecule and the prolonged onset and activity of the drug's effects would mean that it could be administered less frequently. A less frequent and thus more convenient dosing schedule enhances the practical value of the drug as a treatment option.

As would be apparent to a person of skill in the art, the techniques and procedures of Patel et al. are readily adaptable to the delivery of any peptides that fall within a limited size range, including any of the peptides of the present invention. For example, a peptide of the present invention that treats and/or prevents cell proliferative or immunological disorders, such as a fragment of VAPEEHPTLLTEAPLNPK (CMS-010), could be conjugated to the same molecule used by Patel et al. In the treatment of an individual with an infection that affects the brain, the conjugated molecule would allow fragments of VAPEEHPTLLTEAPLNPK (CMS-010) access to the brain from the bloodstream and allow fragments of VAPEEHPTLLTEAPLNPK (CMS-010) to exert their effects on cells or tissues in the brain. Modifications to alter the targeting of the carrier molecule would also be apparent to such a person. The targeting feature of the carrier molecule is a function of the identity of the two amino acids that comprise the dipeptide mask at the end of the fatty acid chains. The Arg-Pro dipeptide interacts preferentially with the set of membrane-bound endopeptidases found on the surface of the blood brain barrier's endothelial membrane. Other endothelial cells and membranes could potentially be targeted by other dipeptide combinations.

Conjugation has also been used by researchers to create peptide drugs that can be effectively absorbed through the digestive tract or transdermally. Any of the conjugation technologies for enhancing absorption described below, as well as other conjugation technologies familiar to those skilled in the art, may be used to enhance the absorption of a peptide that comprises, consists essentially of or consists of a sequence selected from SEQ ID No. 2-31 (wherein said peptide does not comprise the sequence of CMS-010) and functional derivatives thereof. Kramer et al. describe a procedure for the coupling of peptide drugs to bile acids. The absorption rate for the conjugated molecule following oral delivery of the compound is significantly enhanced as compared to the peptide alone (J. Biol. Chem., 269 (14): 10621, 1994). Toth et al. (J. Med. Chem., 42 (19):4010, 1999) describe the conjugation of a peptide drug with anti-tumor properties to lipoamino acids (LAA) or liposaccharides (LS), in order to increase the absorption rate and enhance the delivery of the anti-cancer peptide to its active site. In their study, a derivative of somatostatin that shows strong anti-proliferative properties, but has impaired pharmokinetics, is conjugated to either LAA or LS. The resulting conjugate drug has improved absorption profiles across skin and gut epithelium and increased resistance to degradation while still active against tumor cells. These techniques would be very useful in conjunction with any of the peptides of the present invention. By increasing the rate of absorption of the molecule across the intestinal epithelium, more of the peptide can be delivered to the bloodstream and exert its effect on the individual being treated.

Conjugation may also be used to provide sustained release of a peptide drug. Any of the conjugation technologies for providing sustained release, as well as other conjugation technologies familiar to those skilled in the art, may be used to provide sustained release of a peptide that comprises, consists essentially of or consists of a sequence selected from SEQ ID No. 2-31 (wherein said peptide does not comprise the sequence of CMS-010) and functional derivatives thereof. As seen above in the work of Patel et al., the sustained delivery of a peptide drug can be achieved with conjugation methods. Another example is the work of Kim et al. (Biomaterials, 23:2311, 2002), where recombinant human epidermal growth factor (rhEGF) was conjugated to polyethylene glycol (PEG) before microencapsulation in biodegradable poly(lactic-co-glycolic acid) (PLGA) micro spheres. Microencapsulation in PLGA has been used by several groups to deliver various growth factors and morphogenic proteins (Meinel et al., J. Controlled Rel., 70:193, 2001). Through conjugation to PEG, rhEGF became resistant to forming water-insoluble aggregates and to adsorption to the water-organic phase interface during micelle formation with PLGA as compared to unconjugated, free rhEGF. The pharmokinetics of the formulation with the conjugated hormone were improved, showing longer lasting, steadier and overall greater drug activity than with the free hormone, which the researchers speculate is due to the enhanced physical stability of the hormone conjugated to PEG. A similar strategy could be employed to create sustained release formulations of any of the peptides of the present invention. For example, as seen in Example 1 below, particular fragments and derivatives of VAPEEHPTLLTEAPLNPK (CMS-010) exhibit potent anti-proliferative and immuno-modulatory effects. By conjugating PEG to this peptide and incorporating the conjugated drug into PLGA microspheres, the anti-proliferative and immuno-modulatory effects of fragments and derivatives of VAPEEHPTLLTEAPLNPK (CMS-010) can be longer lasting and more stable, as the dosing of the drug, as it is being released from its PEG conjugate, is more even and ensures a more constant delivery of the peptide drug to the site of infection.

Prolonged release of a peptide drug can significantly enhance its activity. Any of the conjugation technologies for providing prolonged release of a peptide described below, as well as other conjugation technologies familiar to those skilled in the art, may be used to provide prolonged release of a peptide that comprises, consists essentially of or consists of a sequence selected from SEQ ID No. 2-31 (wherein said peptide does not comprise the sequence of CMS-010) and functional derivatives thereof. Oldham et al. (Int. J. Oncology, 16:125, 2000) compares the anticancer agent paclitaxel against a new form of the drug, paxlitaxel conjugated to poly(L-glutamic acid) (PG-TXL). PG-TXL appeared to have superior anti-tumor activity compared to free paclitaxel, suggesting that the drug has superior pharmokinetic properties or maybe even a superior method of action. However, investigators found that PG-TXL exerted its effects by the same mechanism of action as the free drug, inducing cell cycle arrest by disturbing the polymerization of microtubules subunits. Evidence suggests that the superior anti-tumor activity of the conjugated drug arises from a continuous and steady release of the free drug from the conjugate, maintaining its therapeutic concentration for a longer period as compared to administration of the free peptide. The addition of poly(L-glutamic acid) tail to a peptide of the invention with infection-fighting properties could enhance those properties as well.

The enzymatic degradation of peptides may, in some cases, reduce the effectiveness of the peptides as drugs. Any of the conjugation technologies for reducing enzymatic degradation of a peptide described below, as well as other conjugation technologies familiar to those skilled in the art, may be used to reduce the enzymatic degradation of a peptide that comprises, consists essentially of or consists of a sequence selected from SEQ ID No. 2-31 (wherein said peptide does not comprise the sequence of CMS-010) and functional derivatives thereof. Researchers have developed numerous approaches to protect peptides from luminally secreted proteases in the gut as well as membrane-bound peptidases. The latter are found on the surface of all mucosal tissues, the crossing of which is often the route of entry for peptide drugs. Bernkop-Schurch et al. (J. Drug Target., 7:55, 1999) report the creation of peptide drug formulations containing inhibitors of pepsin. An analogue of pepstatin was covalently attached to mucoadhesive polymers; this novel pepsin inhibitor was included in tablets containing insulin. After incubation under laboratory conditions simulating digestion, all of the insulin from control tablets was metabolised, whereas nearly 50% of the insulin from tablets containing the inhibitor was protected from degradation. In another study, the same group utilized protease inhibitors at dosages that would normally cause toxic side effects to inhibit degradation of biologically active peptides (Bernkop-Schnurch et al., Adv. Drug Del. Rev., 52:127, 2001). This approach utilizes chitosan, an aminopolysaccharide related to cellulose that is extracted from chitin, a major structural polysaccharide found in crustaceans and other organisms. By conjugating the protease inhibitors to chitosan and including this conjugated molecule in the formulation of the peptide drug, significant inhibition of digestive tract proteases was seen, increasing the bioavailability of the peptide, without the side effects that would be expected with administration of free protease inhibitors. In the study, a variety of protease inhibitors alone and in combination were utilized for conjugation to the chitosan carrier. A chitosan-EDTA conjugate inhibited endogenous proteases as well, by binding mineral co-factors required by certain proteases for activity. As would be readily apparent to one with skill in the art, a large number of possible combinations between carrier molecules and effector moieties could be created to provide beneficial properties to peptide formulations, any of which could easily be adapted for use with a peptide of the present invention. By creating a formulation for oral delivery of the peptide using protease inhibitors bound to chitosan, oral delivery of a peptide of the invention could be used in place of intramuscular injections. This approach does not rule out using the more absorbable, conjugated version of a peptide that comprises, consists essentially of or consists of a sequence selected from SEQ ID No. 2-31 (wherein said peptide does not comprise the sequence of CMS-010) and functional derivatives thereof (discussed in a paragraph above) in this formulation, to create an even greater level of bioavailability for this peptide and its derivatives.

In addition to being targeted to a location by another molecule, peptides themselves can serve as the molecule that targets. Any of the conjugation technologies for using a peptide to target a molecule to a desired location described below, as well as other conjugation technologies familiar to those skilled in the art, may be used with a peptide that comprises, consists essentially of or consists of a sequence selected from SEQ ID No. 2-31 (wherein said peptide does not comprise the sequence of CMS-010) and functional derivatives thereof. For example, researchers have taken the anticancer drug difluoromethylornithine (DFMO) and conjugated it to a peptide for targeting purposes. DFMO is a highly cytotoxic agent that is effective in killing a variety of tumor cell types. However, since it is rapidly cleared from the body, its therapeutic value is limited. In this study, DFMO has been conjugated to a particular fragment of α melanotropin and an analogue of the fragment containing two amino acid substitutions that was shown to bind preferentially to the melanotropin receptors on a human melanoma cell line (Suli-Vargha et al., J. Pharm. Sci., 86:997, 1997). To facilitate the liberation of DFMO from the peptide fragments by aminopeptidases, the drug was conjugated to the N-terminal ends of the peptides. The researchers found that the conjugated drugs are more effective at killing melanoma cells that the unconjugated drug alone.

The effects of the peptides of the present invention may be due in part to a targeting ability inherent in the peptides themselves. For instance, like the α melanotropin fragment, a particular peptide of the invention may bind to a certain receptor found on the surface of a distinct type of cell. By using that peptide as a conjugant, a drug could be targeted to the location of those cells within the body of an individual being treated with the drug.

Peptides as conjugates can serve functions other than targeting. Any of the conjugation technologies for enhancing the therapeutic effectiveness of a peptide described below, as well as other conjugation technologies familiar to those skilled in the art, may be used to enhance the therapeutic effectiveness of a peptide that comprises, consists essentially of or consists of a sequence selected from SEQ ID No. 2-31 (wherein said peptide does not comprise the sequence of CMS-010) and functional derivatives thereof. Fitzpatrick et al. have improved upon a conjugated anticancer agent by using a peptide spacer between the two molecules (Anticancer Drug Design, 10:1, 1995). Methotrexate had already been conjugated to human serum albumen (HSA) to increase its uptake by and activity against tumor cells. Once taken up by a cell, some of the methotrexate is liberated from the conjugate by enzymes in the lysosome and can then exert its cytotoxic effects. By inserting a four amino acid linker peptide between the methotrexate and the HSA that is easily digested by lysosomal enzymes, the amount of active methotrexate generated within cells from the conjugate molecule was increased. The peptides of the present invention may be exerting their effects through specific interaction with particular enzymes. By incorporating a peptide of the invention into a conjugated molecule as a linker segment between a drug and its carrier molecule, or in addition to another linker segment, the pharmacokinetics can be altered. This can create a prodrug that is more resistant or more susceptible to the activity of proteases, which subsequently decreases or increases the rate of drug molecule release from the conjugate. As seen in the examples of conjugated chemotherapy agents above, altering that rate of drug molecule delivery can greatly enhance the effectiveness of a drug.

The effects of a drug on a particular cell may be altered depending upon other factors such as the activation state of a cell or the presence of other molecular signals near or within the cell. In some cases, in order for a drug to have an effect, another molecule or signal needs to be present. Damjancic et al. (Exp. Clin. Endocrin., 95:315, 1990) studied the effects of human atrial natriuretic peptide (hANP) on patients with deficient endogenous glucocorticoid synthesis. The peptide was given to patients during a withdrawal of glucocorticoid therapy or during subsequent resumption of therapy using dexamethasone. Patients responded to hANP with an increase in diuresis and sodium excretion only when the peptide hormone was given during concomitant dexamethasone treatment. Treatment with hANP during withdrawal of glucocorticoid therapy had no effect. The effect of concurrent steroid hormone administration can also be to enhance the activity of a peptide. In a report from Zhu et al. (Acta Pharm. Sinica, 28:166, 1993), the activity of the analgesic peptide kyotorphin (KTP) was significantly enhanced by conjugation to hydrocortisone via a short linker segment, as compared to the action of the peptide alone. No effect was seen with the administration of hydrocortisone alone.

Figure 2:
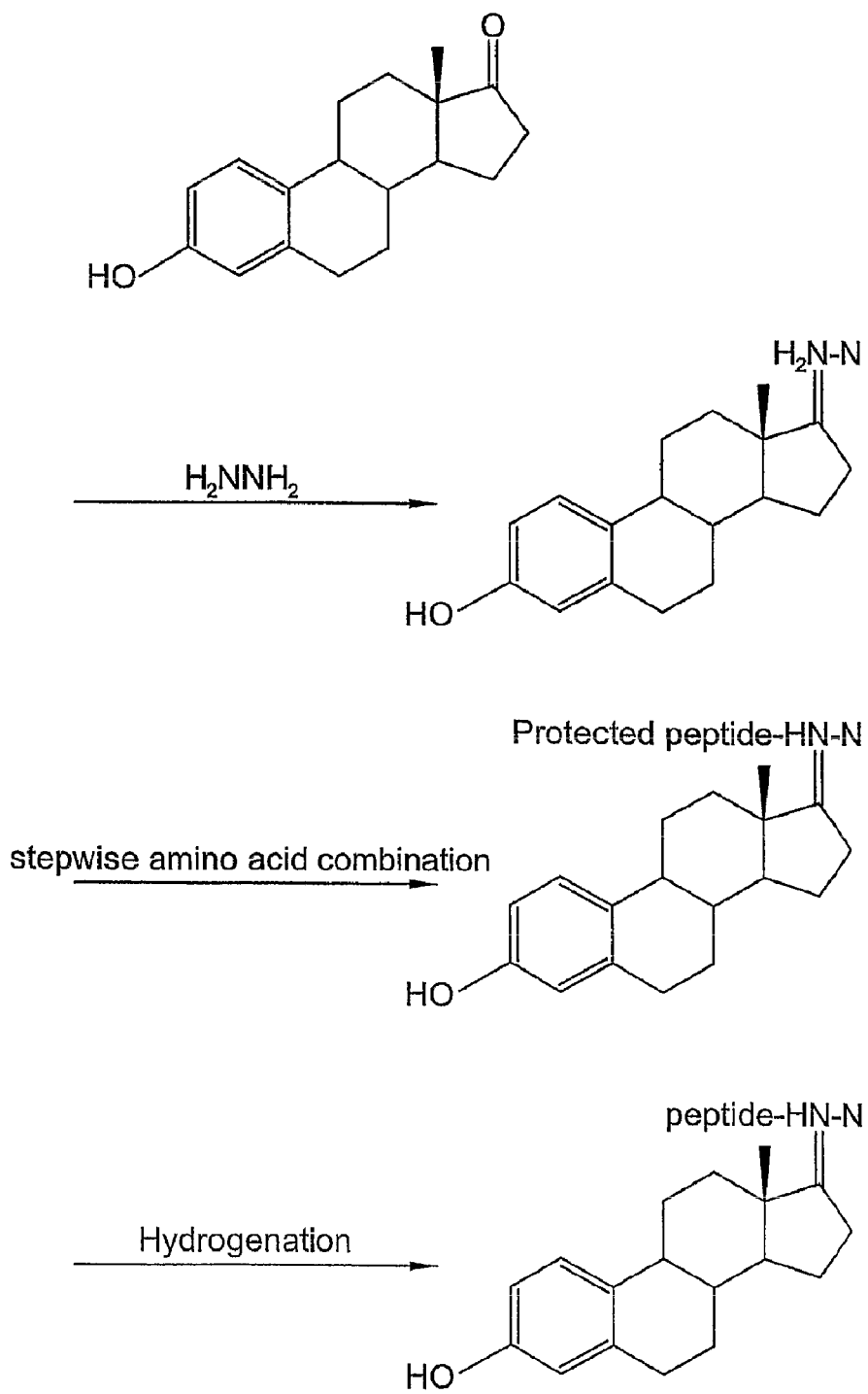
FIG. 2 shows a second, alternative set of reactions for creating the same linkage as in FIG. 1.
Figure 3:
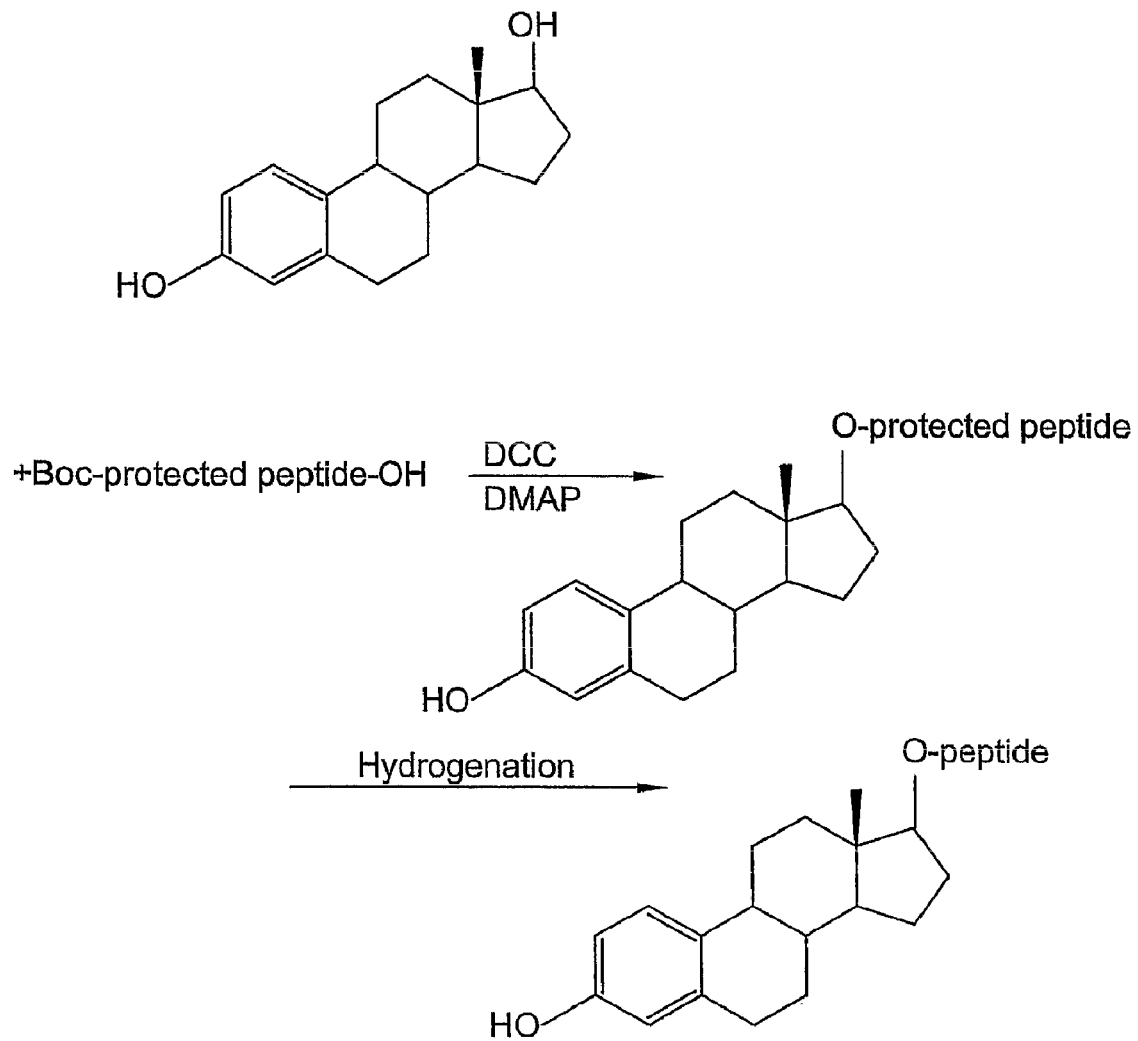
FIG. 3 contains a series of chemical reactions designed to link a peptide to a molecule of estradiol with a covalent bond.
Figure 4:
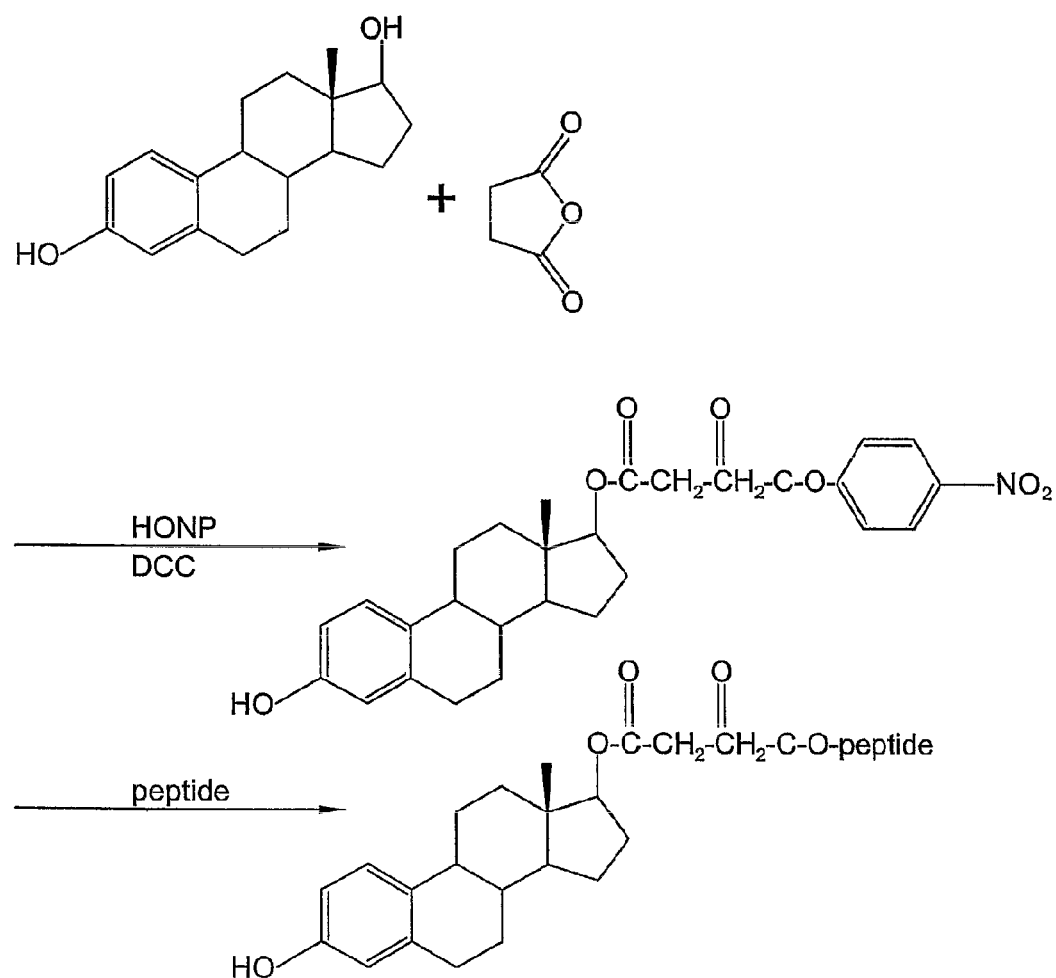
FIG. 4 contains a second series of chemical reactions for creating the same linkage as in FIG. 3.
Figure 5:
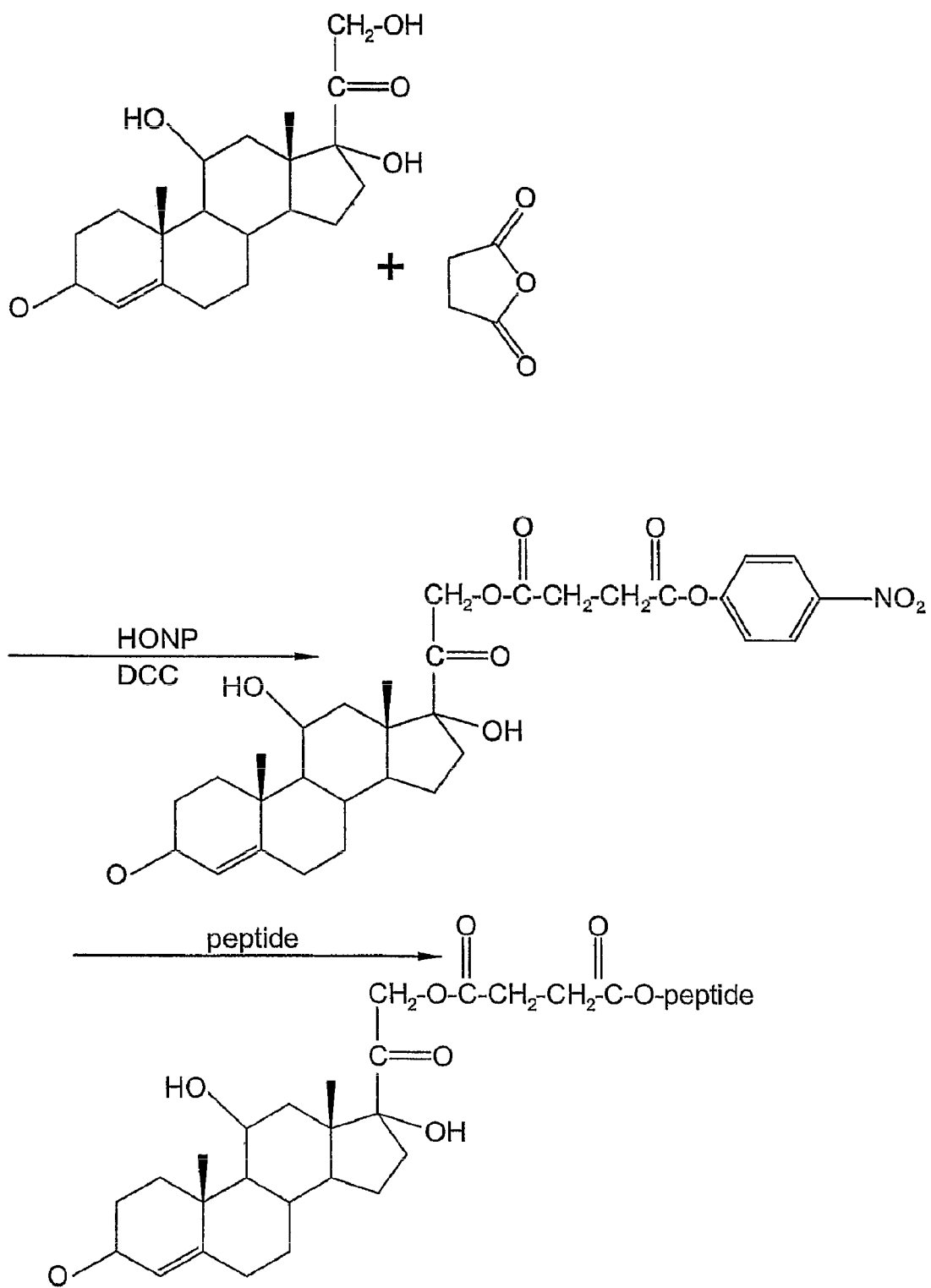
FIG. 5 demonstrates a method of linking a peptide via a covalent bond to a molecule of hydrocortisone.

The results of these studies illustrate the ability of steroid hormones as conjugated molecules or as ingredients in formulations can allow or enhance the activity of biologically active peptides. Any of the peptides of the present invention may also be modulated or activated by conjugation to or co-application of steroid hormones. The techniques of Zhu et al. can be readily adapted for conjugation of steroid molecules to peptide of the present invention. FIGS. 1 through 5 also provide exemplary step-wise synthesis reactions for linking steroid hormones to any of the peptides of the present invention.

The examples presented above provide exemplary ways to augment the usefulness and the activities of any of the peptides of the invention. Further developments in this field will help overcome the barriers to creating effective peptide-based clinical treatments. As would be apparent to one with skill in the art, the techniques, reagents and protocols developed for use in peptide biochemistry, pharmaceutical research and clinical testing are all readily applicable to any of the peptides of the present invention.

EXAMPLES

Background

It was anticipated that within the sequence of VAPEEHPTLLTEAPLNPK (CMS-010), some amino acids can be more important for the bioactivity than the others. In some embodiments of the invention, by finding out the active moiety/moieties within VAPEEHPTLLTEAPLNPK (CMS-010), those amino acids in the sequence that do not contribute to the peptide's activity can be removed so that the bioactive molecule can be made shorter. Recombinations of different active moieties of the peptide can also be done to obtain new peptide molecules having modified bioactivities. The shortening of the bioactive peptide molecule can have both biological and economic significance. By having shorter sequence, the biological properties of the peptide are modified and such modifications may have potential therapeutic advantages, such as modified biological half-life, receptor affinity, or side effect profile. Shorter peptides are also cheaper to produce and can lower the production cost.

In order to determine the active moieties within VAPEEHPTLLTEAPLNPK (CMS-010), we performed a series of truncation experiments. CMS-010 was truncated at each of the peptide bonds from the amino end to the carboxyl end. We anticipate that if an active moiety were truncated, the bioactivity of the resultant pair of peptides would decrease, disappear or be modified in some fashion (activation/inactivation of the bioactivity). After locating the active moiety/moieties within CMS-010, a new set of peptides can be constructed by combinations of the different active moieties.

A set of truncated or recombinant peptides was identified in our experiments as having bioactivities that have potential therapeutic human or biological use. This set of peptides is given in Table 1 below. Our findings are reported in the examples that follow Table 1.

TABLE 1

Truncated and recombinant peptides based on the sequence of CMS-010

| Peptide | Sequence | SEQ ID No. |
| --- | --- | --- |
| CMS-010.02 | APEEHPTLLTEAPLNPK | 2 |
| CMS-010.03 | VAPEEHPTLLTEAPLNP | 3 |
| CMS-010.04 | PEEHPTLLTEAPLNPK | 4 |
| CMS-010.05 | VAPEEHPTLLTEAPLN | 5 |
| CMS-010.07 | VAPEEHPTLLTEAPL | 6 |
| CMS-010.08 | VAPEEHPTLLTEAP | 7 |
| CMS-010.09 | EHPTLLTEAPLNPK | 8 |
| CMS-010.11 | HPTLLTEAPLNPK | 9 |
| CMS-010.12 | VAPEEHPTLLTE | 10 |
| CMS-010.13 | PTLLTEAPLNPK | 11 |
| CMS-010.14 | VAPEEHPTLLT | 12 |
| CMS-010.15 | TLLTEAPLNPK | 13 |
| CMS-010.16 | VAPEEHPTLL | 14 |
| CMS-010.17 | LLTEAPLNPK | 15 |
| CMS-010.18 | VAPEEHPTL | 16 |
| CMS-010.19 | LTEAPLNPK | 17 |
| CMS-010.20 | VAPEEHPT | 18 |
| CMS-010.21 | TEAPLNPK | 19 |
| CMS-010.22 | VAPEEHP | 20 |
| CMS-010.23 | EAPLNPK | 21 |
| CMS-010.24 | APLNPK | 22 |
| CMS-010.25 | VAPEEH | 23 |
| CMS-010.26 | PLNPK | 24 |
| CMS-010.27 | VAPEE | 25 |
| CMS-010.28 | LNPK | 26 |
| CMS-010.29 | VAPE | 27 |
| CMS-010.31 | NPK | 28 |
| CMS-010.32 | VA | 29 |
| CMS-010.103 | VALLT | 30 |
| CMS-010.105 | VANPK | 31 |

Example 1

The Effect of Peptides on Mice T-Lymphocyte Transformation Induced by ConA In Vitro 1.1 Materials 1.1.1 Peptides All amino acids involved were of L form: CS Bio Co., USA 1.1.2 Control and Other Regents Saline: OTSUKA Pharmaceutical Co., Ltd, PR China. RPMI-1640 culture medium and fetal bovine serum (FBS): Gibcol Co., USA. MTT and ConA: Sigma Co., USA 1.2 Animals BALB/c mice (H-$2^d$, SPF, 6-8 weeks old, weight 18-22 g): Military Medical Academy of Science, PR China.

1.3 Method[1]

The spleens from healthy mice were isolated aseptically and manually dispersed in 10% FBS RPMI-1640 solution using an injection needle. The dispersed cell suspension was further sieved through a 100-gauge 150 μm diameter stainless steel sieve. The spleen cell suspension was adjusted to a density of $4 \times 10^6$/ml and was aliquoted onto 96-well cell culture plates at 100 μl/well. Peptides were dissolved in plain RPMI-1640. The design of the groupings was as given below.

Peptide group: 100 μl working peptide solution+75 μl spleen cell suspension+25 μl ConA working solution.

ConA control group: 100 μl RPMI-1640+75 μl spleen cell suspension+25 μl ConA working solution.

Negative control group: 125 μl RPMI-1640+75 μl spleen cell suspension.

The final concentration of ConA in the well was 5 μg/ml. The final concentrations of peptides in the well were 80 μg/ml, 16 μg/ml, 3.2 μg/ml, 0.64 μg/ml, and 0.128 μg/ml. Each peptide group contained three parallel wells, and eight or twelve wells for the control groups. The cells were incubated for 68 hrs at 37° C., 5% $CO_2$. MTT method was used to obtain a reading of $OD_{570}$ nm of each well referenced at 630 nm on an ELISA reader.

1.4 Results

TABLE 2

The effect of peptides on mice T-lymphocyte transformation induced by ConA in vitro.

| Group | Concentration | N | OD |
|---|---|---|---|
| CMS-010.26 | 80 μg/ml | 3 | 0.353 ± 0.016* |
| CMS-010.26 | 16 μg/ml | 3 | 0.356 ± 0.006* |
| CMS-010.26 | 3.2 μg/ml | 3 | 0.332 ± 0.015* |
| CMS-010.26 | 0.64 μg/ml | 3 | 0.348 ± 0.025* |
| CMS-010.26 | 0.128 μg/ml | 3 | 0.354 ± 0.017* |
| CMS-010.105 | 80 μg/ml | 3 | 0.407 ± 0.019* |
| CMS-010.105 | 0.64 μg/ml | 3 | 0.386 ± 0.008* |
| Negative control | — | 12 | 0.134 ± 0.011* |
| ConA control | 5 μg/ml | 12 | 0.467 ± 0.043 |

*compared to the ConA positive control group, P < 0.05

TABLE 3

The effect of peptides on mice T-lymphocyte transformation induced by ConA in vitro

| Group | Concentration | N | OD |
|---|---|---|---|
| CMS 010.32 | 80 μg/ml | 3 | 0.276 ± 0.034* |
| CMS-010.32 | 16 μg/ml | 3 | 0.273 ± 0.023* |
| CMS-010.32 | 3.2 μg/ml | 3 | 0.309 ± 0.030* |
| CMS-010.32 | 0.64 μg/ml | 3 | 0.321 ± 0.048 |
| CMS-010.32 | 0.128 μg/ml | 3 | 0.306 ± 0.033* |
| Negative control | 5 μg/ml | 8 | 0.108 ± 0.012* |
| ConA control | — | 8 | 0.358 ± 0.028 |

*Compared to the ConA positive control group, P < 0.05

1.5 Conclusion

CMS-010.26, CMS-010.32 and CMS-010.105, at suitable concentrations, were found to be able to suppress mice T-lymphocyte transformation induced by ConA in vitro, with statistical significance compared with the ConA positive control (P<0.05).

Example 2

The Effect of Peptides on Mice T-Lymphocyte Transformation and NK Cell Activity In Vivo 2.1 Materials 2.1.1 Peptides All amino acids involved were of L form: CS Bio Co., USA.

2.1.2 Controls and Other Regents

Cyclosporine A: Novartis Pharma AG., Switzerland. Saline: OTSUKA Pharmaceutical Co. Ltd, PR China. RPMI-1640 culture medium and fetal bovine serum (FBS): GIBCOL, USA. MTT and ConA: Sigma Co., USA 2.1.3 Animals BALB/c mice (H-$2^d$, SPF, 6-8 weeks old, weight 18-22 g, 50% female and 50% male): Military Medical Academy of Science, PR China.

2.2 Method 2.2.1 Grouping of Animals and Administration

Animals were randomized into two peptide groups (200 μg/kg/day and 50 μg/kg/day), Cyclosporine A group (10 mg/kg/day), and saline group (0.5 ml/day). Each group contained 10 mice, in which half were female and half were male. All test substances were dissolved in 0.5 ml saline and administered intraperitoneally once per day for 20 days. T-lymphocyte transformation and NK cell activity were examined on the day immediately following the last injection.

2.2.2 T-Lymphocyte Transformation[1-2]

The day after the last test substance administration, the mice were sacrificed by cervical dislocation. The spleens were isolated aseptically and manually dispersed in 10% FBS RPMI-1640 solution using an injection needle. The dispersed cell suspension was further sieved through a 100 gauge 150 μm diameter stainless steel sieve and adjusted to $4 \times 10^6$/ml. The cell suspensions were inoculated onto a 96 wells cell culture plate, 100 μl/well with the following design.

Assay wells: 100 μl cell suspension+100 μl ConA

Control wells: 100 μl cell suspension+100 μl RPMI-1640

Four assay and four control wells were set up for each animal. The plates were incubated at 37° C., 5% $CO_2$ for 68 hours. MTT was then added and the plates read at OD 570 nm referenced at 630 nm with ELISA reader. Stimulation Index SI (%)=(assay well OD/control well OD)×100%.

2.2.3 The Effect of Peptides on NK Cell Activity[3-5].

YAC-1 target cells were brought to log phase and adjusted to a density of $1 \times 10^5$/ml. Mice spleen cells prepared in section 2.2.2 above were adjusted to a density of $4 \times 10^6$/ml and used as effector cells. The cell suspensions were inoculated onto 96 wells cell culture plates as follows:

Effector cell wells: 100 μl spleen cell suspension+100 μl RPMI-1640

Assay wells: 100 μl spleen cell suspension+100 μl YAC-1 cell suspension

Target cell wells: 100 μl YAC-1 cell suspension+100 μl RPMI-1640

Three assay wells and three effector cell wells were set up for each animal, and 12 target cell wells were set up per cell culture plate. The plates were incubated at 37° C., 5% $CO_2$ for 4 hours, then MTT was added and the plates were read at OD 570 nm referenced at 630 nm with ELISA reader. NK cell activity (%)=1−[(assay wells OD−effector cell wells OD)/target cell wells OD]×100%

2.3 Results 2.3.1 Experiment of T-Lymphocyte Transformation

TABLE 4

The effect of peptides on mice T-lymphocyte transformation[1]

| Group | Dosage | N | SI |
|---|---|---|---|
| CMS-010.24 | 50 μg/kg/day | 10 | 2.40 ± 0.31** |
| CMS-010.26 | 200 μg/kg/day | 7 | 2.19 ± 0.59** |
| CMS-010.28 | 200 μg/kg/day | 9 | 2.70 ± 0.37** |
| Saline | 0.5 ml/day | 8 | 3.63 ± 0.69 |

**Compared to saline group, $P < 0.01$

TABLE 5

The effect of peptides on mice T-lymphocyte transformation (2)

| Group | Dosage | N | SI |
|---|---|---|---|
| CMS-010.25 | 200 μg/kg/day | 10 | 2.43 ± 0.69* |
| Saline | 0.5 ml/day | 10 | 3.15 ± 0.83 |

*Compared to saline group, $P < 0.05$

TABLE 6

The effect of peptides on mice T-lymphocyte transformation (3)

| Group | Dosage | N | SI |
|---|---|---|---|
| CMS-010.04 | 50 μg/kg/day | 8 | 1.56 ± 0.25** |
| Saline | 0.5 ml/day | 9 | 2.24 ± 0.52 |

**Compared to saline group, $P < 0.01$

TABLE 7

The effect of peptides on mice T-lymphocyte transformation (4)

| Group | Dosage | N | SI |
|---|---|---|---|
| CMS-010.12 | 50 μg/kg/d | 10 | 2.12 ± 0.42** |
| CMS-010.14 | 50 μg/kg/d | 9 | 2.12 ± 0.51** |
| Saline | 0.5 ml/day | 10 | 2.96 ± 0.61 |

**Compared to saline group, $P < 0.01$ 2.3.2 Experiment of NK Cell Activity

TABLE 8

The effect of peptides on mice NK cell activity[1]

| Group | Dosage | N | NK cell activity (%) |
|---|---|---|---|
| CMS-010.24 | 200 μg/kg/day | 10 | 69.0 ± 7.4* |
| CMS-010.24 | 50 μg/kg/day | 10 | 56.0 ± 6.0** |
| CMS-010.26 | 200 μg/kg/day | 9 | 67.7 ± 5.3** |
| CMS-010.26 | 50 μg/kg/day | 10 | 68.5 ± 7.2* |
| CMS-010.28 | 200 μg/kg/day | 9 | 70.3 ± 6.7* |
| Saline | 0.5 ml/day | 10 | 76.0 ± 4.3 |

*Compared to saline group, $P < 0.05$
**Compared to saline group, $P < 0.01$

TABLE 9

The effect of peptides on mice NK cell activity[2]

| Group | Dosage | N | NK cell activity (%) |
|---|---|---|---|
| CMS-010.11 | 50 μg/kg/day | 9 | 63.5 ± 4.7** |
| CMS-010.13 | 50 μg/kg/day | 10 | 70.9 ± 17.5* |
| CMS-010.14 | 200 μg/kg/day | 8 | 43.1 ± 13.7* |
| CMS-010.14 | 50 μg/kg/day | 9 | 75.3 ± 9.0** |
| Saline | 0.5 ml/day | 10 | 55.3 ± 6.1 |

*Compared to saline group, $P < 0.05$
**Compared to saline group, $P < 0.01$ 2.4 Conclusion At suitable dosages, CMS-010.04, CMS-010.12, CMS-010.14, CMS-010.24, CMS-010.25, CMS-010.26, and CMS-010.28 were found to suppress mice T-lymphocyte transformation in vivo, with statistical significance compared with the saline control ($P<0.05$).

At suitable dosage, CMS-010.24, CMS-010.26, and CMS-010.28 were found to suppress mice NK cell activity in vivo, with statistical significance compared with the saline control ($P<0.05$).

At suitable dosage, CMS-010.11, CMS-010.13, and CMS-010.14 were found to enhance mice NK cell activity in vivo, with statistical significance compared with the saline control ($P<0.05$).

Example 3

The Effect of Peptide on Mice Antibody Formation In Vivo 3.1 Materials 3.1.1 Peptide All amino acids involved were of L form: CS Bio Co., USA.

3.1.2 Controls and Other Reagents

Cyclosporine A: Novartis Pharma AG., Switzerland. Saline: OTSUKA Pharmaceutical Co. Ltd., PR China 3.1.3 Animals BALB/c mice ($H-2^d$, SPF, 6-8 weeks old, weight 18-22 g, 50% female and 50% male): Military Medical Academy of Science, PR China.

3.2 Method 3.2.1 Grouping of Animals and Test Substance Administration

The mice were randomized into three groups: peptide (200 μg/kg/day), Cyclosporine A (10 mg/kg/day), and saline (0.5 ml). Each group contained 12 mice, 6 female and 6 male. The test substances were dissolved in 0.5 ml saline and applied intraperitoneally once per day for 20 consecutive days.

3.2.2 Antibody Raising and Quantification[7]

Sheep red blood cells (SRBC) were resuspended with saline to 2% (v/v) and 0.2 ml of the resuspended cell solution was applied intraperitoneally to each mouse on day 16th of the test substance administration. On the day after the last test substance administration, blood was collected from the inner canthus and left at room temperature for one hour for serum exudation. After centrifugation at 200 g for 10 minutes, the serum was diluted by 200 times with normal saline.

For the preparation of the complement working solution, 10 volumes of fresh Cavy serum was added into one volume of centrifuge-packed SRBC. This mixture was gently shaken for 30 minutes at 4° C. The SRBC were then removed by centrifugation at 200 g for 10 minutes. Ten volumes of normal saline were added to the supernatant to obtain the working complement solution.

For assay of the mice antibody titer, 0.2 ml of 1% SRBC suspension was added to 1 ml diluted ice-cold mouse serum from each mouse. One ml working complement solution was then added and the mixture incubated at 37° C. for 20 minutes. The reaction was terminated by chilling each sample on ice for 10 minutes. The samples were then centrifuged at 200 g for 10 minutes to obtain the supernatant. To 1 ml of this supernatant, 3 ml Drabkin solution was added and left at room temperature for 10 minutes, and then the $OD_{540nm}$ was measured. The reference lysis-50 reading at $OD_{540nm}$ was determined by following the exact procedure as the sample, except replacing half of the SRBC with saline and without the centrifugation removal of the unlysed SRBC. Sample serum index ($HC_{50}$)=$OD_{540nm}$ of sample/lysis-50 $OD_{540nm}$×200

3.3 Results

TABLE 10

The effect of peptide on mice antibody formation

| Group | Dosage | N | $HC_{50}$ |
|---|---|---|---|
| CMS-010.26 | 200 μg/kg/day | 10 | 141.3 ± 29.3* |
| Cyclosporine A | 10 mg/kg/d | 12 | 148.9 ± 21.7* |
| Saline | 0.5 ml/d | 11 | 167.6 ± 21.5 |

*Compared to saline group, P < 0.05

3.4 Conclusion

CMS 010.26 at suitable dosage was found to suppress mice antibody formation in vivo, with statistical significance compared with the saline control group (P<0.05).

Example 4

The Effect of Peptides on the Growth Rate of KM Mice-Transplanted S180 Sarcoma Cells In Vivo 4.1 Materials 4.1.1 Peptides All amino acids involved were of L form: CS Bio Co., USA.

4.1.2 Controls and Other Reagents

Saline: OTSUKA Pharmaceutical Co. Ltd., PR China.
Adriamycin: Zhejiang Haizheng Pharmaceutical Co., Ltd., PR China 4.1.3 Animals Healthy female KM mice (SPF, 6-8 weeks old, weight 18-22 g): Military Medical Academy of Science, PR China 4.2 Method 4.2.1 Grouping of Animals, Test Substance Administration and Tumor Cell Implanting[8]

$S_{180}$ sarcoma cells were transplanted intraperitoneally into KM mice for 6-8 days and the ascites aseptically collected. The cell concentration was adjusted to $1 \times 10^7$ per ml with 10% FBS RPMI-1640, and 0.2 ml cell suspension was injected through the armpit into each KM mice for developing the sarcoma bearing mice model. The $S_{180}$ sarcoma cells transplanted mice were randomized into five groups: peptide (two groups: 50 μg/kg/day and 10 μg/kg/day), Adriamycin (2 mg/kg/day), Cyclophosphamide (40 mg/kg/day), and saline (0.5 ml/day). Intraperitoneal injection of test substances started on the day immediately after tumor transplantation and continued once per day for 20 consecutive days.

4.2.2 Sarcoma Development Determination

On the day after the last test substance administration, the sarcomas were removed from the mice and weighed. The diameters of each sarcoma on the three planes (A, B, C) were measured by a vernier caliper. The volume of the sarcoma was calculated by the formula: V=(⅙)πABC. The tumor growth inhibition index was calculated by the formula:

Tumor growth inhibition index=(tumor weight of control group−tumor weight of treatment group)/tumor weight of control group×100%

4.3 Results

TABLE 11

The effect of peptides on the development of mice-transplanted $S_{180}$ sarcoma cells vivo[(1)].

| Group | Dosage | N | Sarcoma weight |
|---|---|---|---|
| CMS-010.31 | 50 μg/kg/day | 17 | 1.20 ± 1.60* |
| CMS-010.31 | 10 μg/kg/day | 14 | 1.05 ± 1.28* |
| CMS-010.103 | 50 μg/kg/day | 15 | 1.48 ± 1.44* |
| CMS-010.103 | 10 μg/kg/day | 15 | 1.72 ± 1.53* |
| Adriamycin | 2 mg/kg/day | 17 | 1.52 ± 1.75* |
| Saline | 0.5 ml/day | 12 | 5.07 ± 5.46 |

*Compared to normal saline group, P < 0.05

TABLE 12

The effect of peptides on the development of mice-transplanted $S_{180}$ sarcoma cells in vivo[(2)]

| Group | Dosage | N | Sarcoma weight | Sarcoma volume |
|---|---|---|---|---|
| CMS-010.02 | 500 μg/kg/day | 10 | 0.97 ± 0.85* | 0.65 ± 0.67* |
| CMS-010.02 | 250 μg/kg/day | 10 | 0.68 ± 0.72* | 0.36 ± 0.40* |
| CMS-010.03 | 500 μg/kg/day | 10 | 0.33 ± 0.35*@ | 0.27 ± 0.33*@ |
| CMS-010.03 | 250 μg/kg/day | 10 | 0.68 ± 0.46* | 0.31 ± 0.22* |
| CMS-010.04 | 500 μg/kg/day | 10 | 0.62 ± 0.44* | 0.40 ± 0.28* |
| CMS-010.04 | 250 μg/kg/day | 10 | 0.27 ± 0.19*@ | 0.17 ± 0.12*@ |
| CMS-010.05 | 500 μg/kg/day | 10 | 0.47 ± 0.29*@ | 0.34 ± 0.22* |
| CMS-010.05 | 250 μg/kg/day | 10 | 0.56 ± 0.33* | 0.23 ± 0.19*@ |
| CMS-010.07 | 500 μg/kg/day | 10 | 0.52 ± 0.25* | 0.37 ± 0.20* |
| CMS-010.07 | 250 μg/kg/day | 10 | 0.32 ± 0.14*@ | 0.24 ± 0.13*@ |
| CMS-010.08 | 500 μg/kg/day | 10 | 1.05 ± 0.64* | 1.01 ± 0.63 |
| CMS-010.08 | 250 μg/kg/day | 10 | 0.38 ± 0.27*@ | 0.20 ± 0.14*@ |

TABLE 12-continued

The effect of peptides on the development of mice-transplanted $S_{180}$ sarcoma cells in vivo[2]

| Group | Dosage | N | Sarcoma weight | Sarcoma volume |
|---|---|---|---|---|
| CMS-010.09 | 500 μg/kg/day | 10 | 0.85 ± 0.70* | 0.84 ± 0.84 |
| CMS-010.09 | 250 μg/kg/day | 10 | 0.45 ± 0.38*@ | 0.37 ± 0.44* |
| CMS-010.11 | 500 μg/kg/day | 10 | 1.14 ± 0.74* | 0.95 ± 0.54 |
| CMS-010.11 | 250 μg/kg/day | 10 | 0.64 ± 0.31* | 0.63 ± 0.40* |
| CMS-010.13 | 500 μg/kg/day | 10 | 0.73 ± 0.43* | 0.38 ± 0.23* |
| CMS-010.13 | 250 μg/kg/day | 10 | 0.92 ± 0.56* | 0.91 ± 0.59 |
| CMS-010.14 | 500 μg/kg/day | 9 | 0.67 ± 0.70* | 0.56 ± 0.53* |
| CMS-010.14 | 250 μg/kg/day | 10 | 0.44 ± 0.30*@ | 0.29 ± 0.21* |
| CMS-010.15 | 500 μg/kg/day | 10 | 0.68 ± 0.36* | 0.63 ± 0.35* |
| CMS-010.15 | 250 μg/kg/day | 9 | 0.45 ± 0.35*@ | 0.41 ± 0.37 |
| CMS-010.16 | 500 μg/kg/day | 10 | 0.99 ± 0.42* | 0.92 ± 0.36 |
| CMS-010.16 | 250 μg/kg/day | 9 | 0.63 ± 0.47* | 0.61 ± 0.44* |
| CMS-010.17 | 500 μg/kg/day | 10 | 0.91 ± 0.46* | 0.55 ± 0.34* |
| CMS-010.17 | 250 μg/kg/day | 9 | 0.65 ± 0.41* | 0.40 ± 0.24* |
| CMS-010.18 | 500 μg/kg/day | 9 | 0.59 ± 0.48* | 0.58 ± 0.42* |
| CMS-010.18 | 250 μg/kg/day | 9 | 0.44 ± 0.31*@ | 0.27 ± 0.20*@ |
| CMS-010.19 | 500 μg/kg/day | 9 | 0.68 ± 0.68* | 0.40 ± 0.42* |
| CMS-010.19 | 250 μg/kg/day | 10 | 0.41 ± 0.45*@ | 0.46 ± 0.58* |
| CMS-010.20 | 500 μg/kg/day | 10 | 0.59 ± 0.46* | 0.54 ± 0.51* |
| CMS-010.20 | 250 μg/kg/day | 9 | 1.00 ± 0.76* | 0.88 ± 0.77 |
| CMS-010.21 | 500 μg/kg/day | 10 | 0.44 ± 0.22*@ | 0.44 ± 0.21* |
| CMS-010.21 | 250 μg/kg/day | 10 | 0.51 ± 0.29* | 0.44 ± 0.22* |
| CMS-010.22 | 500 μg/kg/day | 10 | 0.85 ± 0.73* | 0.73 ± 0.87 |
| CMS-010.22 | 250 μg/kg/day | 10 | 0.28 ± 0.12*@ | 0.24 ± 0.08*@ |
| CMS-010.23 | 250 μg/kg/day | 9 | 0.27 ± 0.18@ | 0.21 ± 0.15*@ |
| CMS-010.24 | 500 μg/kg/day | 10 | 1.20 ± 0.79* | 0.62 ± 0.47* |
| CMS-010.24 | 250 μg/kg/day | 10 | 0.61 ± 0.39* | 0.36 ± 0.30* |
| CMS-010.25 | 500 μg/kg/day | 10 | 0.52 ± 0.38* | 0.26 ± 0.21*@ |
| CMS-010.25 | 250 μg/kg/day | 9 | 0.65 ± 0.53* | 0.48 ± 0.37* |
| CMS-010.27 | 500 μg/kg/day | 9 | 1.05 ± 0.86* | 0.51 ± 0.33* |
| CMS-010.27 | 250 μg/kg/day | 10 | 0.78 ± 0.68* | 0.58 ± 0.58* |
| CMS-010.29 | 500 μg/kg/day | 10 | 0.55 ± 0.41* | 0.40 ± 0.11* |
| CMS-010.29 | 250 μg/kg/day | 10 | 1.24 ± 0.72* | 1.02 ± 0.66 |
| CMS-010.31 | 500 μg/kg/day | 10 | 0.78 ± 0.89* | 0.43 ± 0.50* |
| CMS-010.31 | 250 μg/kg/day | 10 | 0.27 ± 0.19*@ | 0.25 ± 0.20*@ |
| CMS-010.32 | 500 μg/kg/day | 10 | 0.41 ± 0.35*@ | 0.40 ± 0.31* |
| CMS-010.32 | 250 μg/kg/day | 10 | 0.38 ± 0.24*@ | 0.25 ± 0.14*@ |
| Cyclophosphamide | 40 mg/kg/day | 10 | 1.07 ± 0.80* | 0.76 ± 0.66* |
| Saline | 0.5 ml/day | 10 | 1.87 ± 0.52 | 1.20 ± 0.28 |

*Compared to normal saline group, P < 0.05
@Compared to Cyclophosphamide group, P < 0.05

4.4 Conclusion

CMS-010.103, CMS-010.02, CMS-010.03, CMS-010.04, CMS-010.05, CMS-010.07, CMS-010.08, CMS-010.09, CMS-010.11, CMS-010.13, CMS-010.14, CMS-010.15, CMS-010.16, CMS-010.17, CMS-010.18, CMS-010.19, CMS-010.20, CMS-010.21, CMS-010.22, CMS-010.23, CMS-010.24, CMS-010.25, CMS-010.27, CMS-010.29, CMS-010.31, and CMS-010.32, at suitable dosages, were found to suppress the development of KM mice-transplanted $S_{180}$ sarcoma cells in vivo, with statistical significance compared with the normal saline control group (P<0.05).

Example 5

The Effect of Peptides on Masugi Nephritis in Rabbits 5.1 Materials 5.1.1 Peptides All amino acids involved were of L form: CS Bio Co., USA.

5.1.2 Controls and Other Reagents

Dexamethasone Sodium Phosphate Injection: Tianjin Jinyao Aminophenal Ltd., PR China. Saline: OTSUKA Pharmaceutical Co. Ltd., PR China. BCG vaccine: Beijing Institute of Biological Products, PR China. Lanolin: Tianjin sixth chemical product factory, PR China. Liquid paraffin: Tianjin sixth chemical product factory, PR China. Diagnostic Reagent for serum BUN: BECKMAN443350, USA. Diagnostic Reagent for serum Creatinine: BECKMAN 443340, USA.

5.1.3 Animals

One male sheep (8 months old): Department of Laboratory Animal, Tianjin Medical University, PR China. Rabbits (MDA, male, 2-2.5 kg): Beijing Fuhao Breed Farm, PR China.

5.2 Methods[9-10]

5.2.1 Preparation of Sheep Anti-Rabbit Renal Cortex Antiserum 5.2.1.1 Preparation of Rabbit Renal Cortex Antigen A healthy rabbit was anesthetized with 4 ml/kg 25% urethane by auricular vein intravenous injection, and intravenously injected with heparin at 1250 U/kg for systemic heparinization. The rabbit abdomen was opened aseptically and the renal arteries and veins were exposed. The renal arteries were catheterized and the renal veins severed. The kidneys were douched with saline until the renal tissue turned grey. The kidneys were then extirpated. The renal cortex was isolated and homogenized in 0.5 volumes of ice-cold saline, and then stored at −20° C.

5.2.1.2 Preparation of Sheep Antiserum 7.5 ml of the renal cortex homogenate was mixed with 2.5 ml of Freund's complete adjuvant (Lanolin to liquid paraffin in a ratio of 1:5, with 5 mg/ml BCG vaccine). After complete emulsification, the antigen was injected into a sheep at five different dorsal locations, 1 ml per location, once every two weeks, for a total of three rounds of injections. Starting with the fourth immunization, 5 g renal cortex was homogenized with one volume of saline and intramuscularly injected into 5 locations on the sheep, 1 ml per location, once every two weeks. The sheep anti-rabbit renal cortex antibody titer was monitored by double immunodiffusion on a bi-weekly basis. When the titer reached 1:32, the sheep antiserum was collected from the carotid artery. The sheep antiserum was mixed with an equal volume of rabbit red blood cells and placed at 4° C. for 12 hours for the removal of anti-rabbit red blood cell antibody. Then the antiserum was collected by centrifugation and placed at 56° C. to inactivate complement and proteases. The antiserum was stored at −20° C.

5.2.2 Grouping of Animals, Test Substance Administration, and Masugi Nephritis Model Establishment Twenty-two healthy rabbits were randomized into 5 groups: peptide (107.3 μg/kg/day and 58.5 μg/kg/day, 4 rabbits per group), dexamethasone (0.1 mg/kg/day, 4 rabbits), saline treatment (1 ml/day, 7 rabbits), and normal healthy (3 rabbits). Before the establishment of a disease state in the rabbits, measurements of serum BUN, creatinine, and urine protein over 24 hours were taken for each rabbit. If there was no abnormality in these measurements, the Masugi nephritis model was established in experimental rabbits by intravenous injection of sheep anti-rabbit renal cortex antiserum via the auricular vein, 0.5 ml per injection, one injection every 30 minutes, for a total of 4 injections per rabbit. The normal healthy (control) rabbit group was injected with saline in the same manner. Intravenous administration of the test substances via the auricular vein was started on the day after the injection of the antiserum, once per day, 1 ml per injection, for 30 consecutive days.

5.2.3 Therapeutic Effect Monitoring

5.2.3.1 Quantification of Urine Protein

Urine was collected from each rabbit over a 24 hour period once per week and the protein content determined by the sulfosalicylic acid method.

5.2.3.2 Pathological Examination

For observation of the effects of peptides on the clearance of sheep anti-rabbit renal cortex IgG antibody from Masugi nephritis rabbits, on the day after the last test substance administration, the rabbits were sacrificed by suffocation and the right kidney was extirpated, freeze-edged and then immunofluorescently stained for the presence of sheep IgG. The fluorescence-positive area of each glomerulus was counted. Thirty glomeruli per rabbit were examined and the average positive area per glomerulus was calculated.

5.2.3.3 Statistics

Statistical significance was determined by the t-test of the SPSS software.

5.3 Results

TABLE 13

Effect of peptide on proteinuria of Masugi nephritis rabbits (mg/dl)

| Group | Dosage/day | N | Week 0 | Week 1 | Week 2 | Week 3 | Week 4 |
|---|---|---|---|---|---|---|---|
| CMS-010.26 | 107.3 µg/kg | 4 | 9.84 ± 4.29 | 187 ± 184 | 114 ± 145 | 26 ± 24* | 28 ± 32* |
| CMS-010.26 | 58.5 µg/kg | 4 | 9.53 ± 4.64 | 77 ± 62 | 150 ± 123 | 20 ± 12* | 36 ± 16* |
| Dexamethasone | 0.1 mg/kg | 4 | 9.48 ± 8.46 | 29 ± 12 | 13.6 ± 6.3* | 13.7 ± 3.1* | 25 ± 19 |
| Saline treatment | 0.5 ml | 7 | 11.72 ± 3.18 | 122 ± 91 | 160 ± 138 | 145 ± 33 | 157 ± 71 |
| Normal healthy | — | 3 | 23.43 ± 18.42 | 7.7 ± 2.0* | — | 6.9 ± 4.5* | 24 ± 7* |

*Compared to saline treatment group, P < 0.05

TABLE 14

Effect of peptide on the clearance of sheep anti-rabbit renal cortex IgG antibody from the Masugi nephritis rabbits

| Group | Dosage/day | N | Positive area count/glomerulus |
|---|---|---|---|
| CMS-010.26 | 107.3 µg/kg | 5 | 5.6 ± 1.2** |
| CMS-010.26 | 58.5 µg/kg | 4 | 6.3 ± 1.4** |
| Dexamethasone | 0.1 mg/kg | 4 | 7.5 ± 1.0 |
| Saline treatment | 0.5 ml | 7 | 8.7 ± 0.9 |
| Normal healthy | — | 3 | — |

**Compared to saline treatment group, P < 0.01

5.4 Conclusion

CMS-010.26 was found to be able to decrease the severity of proteinuria and promote the clearance of sheep anti-rabbit renal cortex antibody in Masugi nephritis rabbits in vivo, with statistical significance compared with the saline treatment control group, P<0.05.

Example 6

The Effect of Peptides on Heymann Nephritis Rats In Vivo

6.1 Materials

6.1.1 Peptide

All amino acids used were of L form: CS Bio Co., USA.

6.1.2 Controls and Other Reagents

Dexamethasone Sodium Phosphate Injection: Tianjin Jin-yao Aminophenal Ltd., PR China. Saline: OTSUKA Pharmaceutical Co. Ltd., PR China. BCG vaccine: Beijing Institute of Biological Products. Lanolin: Tianjin sixth factory of chemical product, PR China. Liquid paraffin: Tianjin sixth factory of chemical product, PR China. Diagnostic reagent for serum BUN: BECKMAN 443350, USA. Diagnostic reagent for serum creatinine: BECKMAN 443340, USA.

6.1.3 Animals

Wistar rats (SPF, 6-8 weeks old, weight 150-200 g): Beijing Vital River Laboratory Animal Co., Ltd., PR China.

6.2 Methods[11-12]

6.2.1 Preparation of Rat Renal Homogenate

Healthy Wister rat abdomens were opened aseptically. The portal vein and inferior vena cava were exposed. The portal vein was catheterized and the inferior vena cava severed. The kidneys were douched by saline until the renal tissue turned gray. The kidneys were extirpated and the renal cortex isolated. The renal cortex was then homogenized on ice and stored −20° C.

6.2.2 Preparation of Rat Renal Cortex Antigen

Lanolin was mixed with liquid paraffin in a 1:2 v/v ratio, heated to 70° C. with shaking, and then autoclaved. Sufficient BCG vaccine was added to the lanolin/paraffin mixture to produce a vaccine concentration of 3 mg/ml to form Freund's complete adjuvant. The renal cortex homogenate, Freund's complete adjuvant, and saline were mixed in a 1:1:2 ratio with mortaring until completely emulsified.

6.2.3 Grouping of Animals and Model Establishment 20 healthy Wistar rats were randomized into two groups: peptide (200 µg/kg/day) and saline treatment (2 ml/day). Two ml of antigen were intraperitoneally injected to each rat, once every two weeks, for a total of 5 rounds of injection. Test substance administration by intraperitoneal injection was started on the day after the third immunization, once per day until the end of the experiment.

6.2.4 Efficacy Monitoring

6.2.4.1 Quantification of Urine Protein

Quantification of uriner protein began at the third week of model establishment. A urine sample was collected from each rat over a 24 hour period once every two and the urine protein content quantified by the sulfosalicylic acid method.

6.2.5 Statistics

Sample values were compared by t-test using SPSS software.

6.3 Results

TABLE 15

Effect of peptide administration on 24 hr. urine protein concentration (mg/dl) of rats with Heymann nephritis

| Group | N | Week 3 | Week 5 | Week 7 | Week 9 |
|---|---|---|---|---|---|
| CMS-010.26 | 10 | 6.2 ± 2.3 | 3.1 ± 1.4 | 3.9 ± 1.6* | 3.8 ± 2.2* |
| Saline treatment | 10 | 4.1 ± 1.3 | 3.1 ± 0.8 | 10.9 ± 2.8 | 12.6 ± 1.2 |

*Compared to saline group, P < 0.05

6.4 Conclusion

At suitable dosage, CMS-010.26 was found to decrease the severity of proteinuria in Heymann nephritis rats in vivo, with statistical significance compared to the saline treatment group (P<0.05).

REFERENCES FOR EXAMPLES 1-6

1. Shuyun Xu, Rulian Bian, Xiu Chen. Methodology of pharmacological experiment. People's Health Publishing House. 2002, 1:1426-1428
2. Principles of Pre-clinical Research of New Drugs, People's Republic of China. 1993, 7:134-135
3. Shuyun Xu, Rulian Bian, Xiu Chen. Methodology of pharmacological experiment. People's Health Publishing House. 2002, 1:1429
4. Jinsheng He, Ruizhu Li, Tingyi Zong. The study on MTT reduction method of testing NK cell activity. China Immunology Journal. 1996, 1 (6): 356-358
5. Principles of Pre-clinical Research of New Drugs, People's Republic of China. 1993, 7:128-129
6. Yuanpei Zhang, Huaide Su. Pharmacological experiment (second edition). People's Health Publishing House. 1998, 137-138
7. Shuyun Xu, Rulian Bian, Xiu Chen. Methodology of pharmacological experiment. People's Health Publishing House. 2002, 1:1429
8. Principles of Pre-clinical Research of New Drugs, People's Republic of China. 1993, 7:137-139
9. Principles of Pre-clinical Research of New Drugs, People's Republic of China. 1993, 7:96
10. Shuyun Xu, Rulian Bian, Xiu Chen. Methodology of pharmacological experiment. People's Health Publishing House. 2002, 1:1227-1228
11. Principles of Pre-clinical Research of New Drugs, People's Republic of China. 1993, 7:97
12. Shuyun Xu, Rulian Bian, Xiu Chen. Methodology of pharmacological experiment. People's Health Publishing House. 2002, 1:1227

Example 7

Delivery of Peptides Through Genetically Engineered *Lactobacillus* Bacterial Species The following is provided as one exemplary method to deliver peptides of this invention to a host as described above. A DNA sequence that encodes a peptide selected from the group consisting of fragments of CMS-010 (VAPEEHPTLL-TEAPLNPK) (wherein said fragments do not comprise the sequence of CMS-010) and functional derivatives thereof is synthesized by chemical means and this DNA sequence is inserted into an expression vector using standard techniques of genetic engineering familiar to those skilled in the art. The expression vector selected contains a constitutive promoter functional in *Lactobacilli*, a multiple cloning site for the introduction of DNA sequences in a specific 5' to 3' orientation as well as a selectable marker gene that confers resistance to an antibiotic (to aid in cloning procedures) and may comprise other sequences to assist in the production and/or secretion of the peptides, such as signal peptide sequences. An example of such a vector is provided by U.S. Pat. No. 5,592,908, to Pavla, which is incorporated herein by reference in its entirety. Briefly, this patent discusses several known promoters that function in *Lactobacillus* species, as well as a method for discovering novel promoters in said bacteria, any of which may be operably linked to a nucleic acid encoding a peptide of the present invention to express the peptide in *Lactobacilli*. A nucleic acid encoding a signal peptide, such as peptides comprising of 16 to 35 mostly hydrophobic amino acids that are active in *Lactobacillus* lactis described in U.S. Pat. No. 5,529,908, cited above, is interposed between the promoter and the nucleic acid encoding the peptide of the present invention such that the nucleic acid encoding the signal peptide is in frame with the nucleic acid encoding the peptide of the present invention.

In addition to the coding sequence of the peptide, the DNA sequence synthesized may comprise sequences to aid in the ligation and cloning of said DNA into the expression vector. For example, restriction enzyme recognition sites that correspond to ones found in the multiple cloning site of the vector can be incorporated into the synthesized DNA at the 5' and 3' ends of the sequence, so that the sequence can be cloned in proper orientation within the vector. Both the vector and the synthesized DNA are digested with the particular restriction enzymes, then purified. Ligation reactions with the vector and the synthesized DNA are followed by transformation into a suitable strain of *E. Coli*. The transformed bacteria are plated on media containing the antibiotic to which the vector confers resistance. A colony of transformed bacteria is selected for growth cultures and plasmid preparation procedures; the presence of the synthesized DNA in the correct orientation is confirmed.

This expression vector is then transformed into a bacterial host cell of a *Lactobacillus* species, such as *L. acidophilus*. Transformed cells are selected for by virtue of the selectable marker found within the vector sequence and the secretion of the peptide may be verified by performing a western blot, performing gel electrophoresis of peptides present in the growth medium or other standard techniques. A transformed colony of bacteria is chosen and used to prepare large-scale cultures of the genetically engineered bacteria. A culture of the genetically engineered bacteria expressing the desired peptide is grown up and at least a portion thereof is administered to the alimentary canal, vagina, trachea or other area of the host organism in which the bacteria are able to replicate. If desired, the bacterial cultures can be treated in a variety of ways to produce a supplement for enteric consumption by the host. These treatments include lyophilization or other methods of preserving the bacteria, in addition to combining the bacteria with carrier agents, such as solutions, solvents, dispersion media, delay agents, emulsions and the like. The use of these agents to prepare supplements is well known in the art. For example, the bacteria can be used to make cultured milk products or other foodstuffs for human consumption, such that the organism expressing the peptide colonizes the gut of the host organism. A number of different methods for incorporating specific strains of lactic acid bacteria into foodstuffs such as yoghurt, kimchee, cheese and butter are disclosed in U.S. Pat. No. 6,036,952, to Oh, which is incorporated herein by reference in its entirety. Upon consuming the bacteria through one of any number of routes, the engineered organisms can colonize the gut and allow the presentation and/or absorption of the peptides of this invention via the mucosal layer of the gut.

Example 8

Delivery of Peptides Through a Genetically Engineered Form of *Bacillus subtilis*

The following is provided as another exemplary method to deliver peptides of this invention to a host as described above. A DNA sequence that encodes a peptide selected from the group consisting of fragments of CMS-010 (VAPEEHPTLL-TEAPLNPK) (wherein said fragments do not comprise the sequence of CMS-010) and functional derivatives thereof is synthesized by chemical means and this DNA sequence is inserted into an expression vector via techniques of genetic engineering, all techniques being known in the art. The expression vector selected comprises a shuttle vector, such as pTZ18R (Pharmacia, Piscataway, N.J.), capable of being propagated in both *E. Coli* and *B. Subtilis* and containing an antibiotic resistance gene for selecting colonies of transformed bacteria. This vector can contain a constitutive promoter active in *B. subtilis*, such as a promoter derived from the Sac B gene of *B. subtilis* as well as a nucleotide sequence encoding a signal peptide active in *B. subtilis* that directs efficient export of expressed heterologous proteins from the bacterial cell. An example of such a vector is disclosed in U.S. Pat. No. 6,268,169, to Fahnestock, the disclosure of which is incorporated herein by reference in its entirety. Briefly, as detailed above, the DNA encoding a peptide of this invention will be synthesized with restriction enzymes sites and/or other sequences to facilitate cloning of the DNA through techniques familiar to those with skill in the art. After transformation into *E. Coli*., plating, selection and propagation of the plasmid to create a plasmid stock, the plasmid is then be transformed into *B. subtilis* and transformants are selected by virtue of resistance to an antibiotic in the plating media.

Peptide production in and secretion from the genetically engineered *B. subtilis* is verified using techniques well known to those with skill in the art, such as radiolabeling of peptides for autoradiographic detection after SDS-PAGE analysis or Western blotting.

A culture of genetically engineered bacteria is grown up and at least a portion thereof is administered to the alimentary canal, vagina, trachea or other area of the host organism in which the bacteria are able to replicate.

Example 9

Delivery of Peptides Through Genetically Engineered *Saccharomyces* Yeast Species The following is provided as another exemplary method to deliver peptides of this invention to a host as described above. A DNA sequence that a peptide selected from the group consisting of fragments of CMS-010 (VAPEEHPTLLTEA-PLNPK) (wherein said fragments do not comprise the sequence of CMS-010) and functional derivatives thereof is synthesized by chemical means and this DNA sequence is inserted into an expression vector via techniques of genetic engineering, all techniques being known in the art. The expression vector selected comprises a stably maintained yeast protein expression vector, comprising a constitutive yeast promoter such as pADH1, sites for replication of the vector in both yeast and *E. Coli*, a gene or genes that confer prototrophy to an auxotrophic yeast mutant for selection purposes, a multiple cloning site (MCS) and, if desired, sequences that code for a signal peptide. Vectors such as this are commercially available and well known in the art or can be readily constructed using standard techniques After insertion of the synthesized DNA into the yeast vector, transformation into *E. Coli*, plating of transformed *E. Coli* onto selective media, selection of a transformed bacterial colony and preparation of plasmid DNA from a growth culture of bacteria from said colony, the vector is transformed into *Saccharomyces cerevisiae* via well-known techniques such as lithium acetate transformation or electroporation. The strain of *Saccharomyces cerevisiae* selected for transformation is a mutant auxotrophic strain that will require a gene on the plasmid in order to grow on minimal media plates. Transformed yeast colonies are isolated by plating the yeast on growth media lacking the gene provided on the vector. Only those yeast that have received the vector and its selective gene and are expressing that gene product will be able to grow into colonies on the minimal media. Verification of peptide secretion can be obtained by performing a Western blot, performing gel electrophoresis of peptides present in the growth medium or other standard techniques.

A transformed colony of yeast is chosen and used to prepare large scale cultures. A culture of the genetically engineered yeast expressing the desired peptide is grown up and at least a portion thereof is administered to the alimentary canal, vagina, trachea or other area of the host organism in which the bacteria are able to replicate. If desired, the yeast cultures can be treated in a variety of ways to produce a supplement for enteric consumption by the host. These treatments include lyophilization or other methods of preserving yeast, in addition to combining the bacteria with carrier agents, such as solutions, solvents, dispersion media, delay agents, emulsions and the like. The use of these agents to prepare supplements is well known in the art. In another embodiment, the transformed yeast are used in the creation of food products, such as fermented milk products like yoghurt and kefir, by techniques known to those skilled in the art. As with live lactic acid bacterial cultures in these foodstuffs, the transformed yeast colonize the gut at least transiently and serve to present peptides to the host via the gut lumen.

Example 10

Targeting of a Peptide to a Particular Location

The following is provided as an exemplary method to selectively deliver a peptide of this invention to a particular compartment, organ, cell type or location within the body. In this case, a cell proliferative disorder is treated by targeting a peptide selected from the group consisting of fragments of CMS-010 (VAPEEHPTLLTEAPLNPK) (wherein said fragments do not comprise the sequence of CMS-010) and functional derivatives thereof to tissues in the kidney of an individual. For example, fragments of CMS-010 (VAPEEHPTLLTEAPLNPK) (wherein said fragments do not comprise the sequence of CMS-010) and functional derivatives thereof are linked by covalent bonds via chemical reactions known in the art to low molecular weight (LMW) lysozyme, a commercially available protein moiety that concentrates specifically in renal tissue. Techniques for achieving conjugation of molecules to LMW lysozyme are documented (Folgert et al., Br. J. Pharmcology, 136:1107, 2002). General techniques for conjugating proteins or peptides to one another are also taught in the literature of the field (Fischer et al., Bioconj. Chem., 12:825, 2001). The newly created conjugated peptide sample is then purified away from chemical reagents used in the linking process by chromatography methods such as cation exchange FPLC and/or gradient centrifugation. Once purified, the conjugated peptide is administered to an individual in need of therapy for nephritic cell proliferative disorder. For its anti-proliferative activity, fragments of CMS-010 (VAPEEHPTLLTEAPLNPK) (wherein said fragments do not comprise the sequence of CMS-010) and functional derivatives thereof are preferentially targeted to renal tissue by virtue of the link between them and the LMW lysozyme, which is selectively concentrated in renal tissue by virtue of the affinity of the LMW lysozyme for the cells of the proximal tubules of the kidney. This preferential delivery allows a greater anti-proliferative effect compared to that of a molar equivalent amount of fragments of CMS-010 (VAPEEHPTLLTEAPLNPK) (wherein said fragments do not comprise the sequence of CMS-010) and functional derivatives thereof by themselves. Inversely, it can reduce the amount of peptide drug required to achieve a certain level of anti-proliferative activity.

Example 11

Enhancing the Delivery of a Peptide to its Active Site

The following is presented as an exemplary method to increase the delivery of a neuroactive peptide to the brain. A peptide of the present invention that exerts its effects on receptors expressed by neurons of the brain is synthesized by chemical methods known to those with skill in the art. Alternatively, it can be expressed by an engineered microorganism and recovered from a culture of such organisms, as detailed in examples above. Once obtained in a purified form, the peptide is utilized in a series of organic chemical reactions to create a triglyceride ester conjugated moiety, attached to the peptide. The conjugated moiety consists of a quaternary substituted carbon center joined to the peptide of the invention through an amide bond with the terminal carboxyl carbon of the peptide. The other three groups attached to the quarternary carbon center consist of carbon ester linkages to 16 carbon fatty acid chains. The fatty acid chains themselves end in terminal dipeptide group, known as a peptide mask, which makes the chains more hydrophilic and targets them to the blood-brain barrier's endothelial cell membrane specifically. The procedure for this synthesis is explained at length in Patel et al., Bioconjugate Chem., 8 (3):434, 1997, and utilizes common reagents and equipment familiar to those with skill in the art.

Once introduced into an individual at a peripheral location, the compound travels throughout the body via the circulatory system, interacting with the endothelial membrane of the blood brain barrier. Step-wise degradation of the dipeptide mask and the lipid chains during the transport of the molecule across the epithelial layer of the blood-brain barrier results in the release of the peptide of the invention into the brain compartment. There the peptide can interact with receptors on the surface of neurons to exert its effect on brain function. The time required for the drug to reach the blood brain barrier and be transported to the brain, with the concomitant degradation of the carrier moiety, alters the kinetics of the drug's activity, creating a more stable and longer lasting effect as compared to the intracerebro ventricular injection of the free peptide.

Example 12

Creating Peptide Formulations that are Resistant to Enzymatic Degradation

The following is provided as an exemplary method for creating a formulation of a biologically active peptide for oral administration that is resistant to the activity of proteases and peptidases found in and along the surface of the digestive tract. In this example, a peptide selected from the group consisting of fragments of CMS-010 (VAPEEHPTLLTEAPLNPK) (wherein said fragments do not comprise the sequence of CMS-010) and functional derivatives thereof is utilized in the making of a pharmaceutical formulation for oral administration to a patient. As described in Larionova et al. (Int. J. Pharma., 189:171, 1999), the peptide is used in the creation of microparticles with soluble starch and a protease inhibitor, aprotinin, that is a strong inhibitor of a variety of luminally secreted and brush border membrane-bound proteases. Briefly, soluble starch, the protease inhibitor aprotinin and the peptide of the invention are dissolved in an aqueous buffer. The ratios of soluble starch, aprotinin, and peptide are determined by experimental methods familiar to one with skill in the art; for example, Larionova et al. utilized in vitro simulated digestion assays to determine the ratios and preparation conditions most effective for the protein used in their study. The aqueous solution is emulsified under mechanical agitation in cyclohexane (1:3 ratio, v/v) containing 5% Span-80, a non-ionic surfactant. A terephthaloyl chloride solution in chloroform is added to the emulsion and stirring is continued 30 minutes, during which the starch molecules are cross-linked with the aprotinin and the peptide. The microparticles created in that process are washed with sequentially with cyclo-hexane, a 95% ethanol solution with 2% v/v Tween 85 detergent, 95% ethanol and water. The microparticles are resuspended in water and lyophilized. The lyophilized compound can be placed into gelatin capsules for oral delivery to the individual in need of treatment.

Once ingested, the compound is released as the gelatin capsule dissolved. The microparticles are broken down in the small intestine by the action of $\alpha$ amylase on the starch molecules, leading to the gradual release of aprotinin and the peptide of the invention. The concurrent release of the potent protease inhibitor aprotinin at the same time and location of the peptide decreases the enzymatic degradation of the peptide and increases the proportion of intact peptide available for absorption through the gut membrane.

While the present invention has been described using the aforementioned methods and data and the specific examples of fragments of the CMS-010 peptide (VAPEEHPTLLTEAPLNPK) and functional derivatives thereof in some cases, it is understood that this is an example only and should not be taken as limitation to the present invention. It should also be understood that fragments of CMS-010 (VAPEEHPTLLTEAPLNPK) (wherein said fragments do not comprise the sequence of CMS-010) and functional derivatives thereof represents particular embodiments of the present invention and the same principle of the present invention can also apply to other functionally equivalent peptides that have been modified without affecting the biological function of fragments of CMS-010 (VAPEEHPTLLTEAPLNPK) (wherein said fragments do not comprise the sequence of CMS-010) and functional derivatives thereof. For example, equivalents of peptide fragments of CMS-010 (VAPEEHPTLLTEAPLNPK) (wherein said fragments do not comprise the sequence of CMS-010) and functional derivatives thereof include those that have conservative amino acid substitutions (i.e. any one of the V, A, P, E, H, L, A, N, K or T, replaced by another amino acid having a residue within the same biochemical type such as hydrophobic, hydrophilic, positive or negatively charged groups). Another example of an equivalent peptide to peptide fragments of CMS-010 (VAPEEHPTLLTEAPLNPK) (wherein said fragments do not comprise the sequence of CMS-010) and functional derivatives thereof is a slightly longer peptide, such as one or two amino acids longer, that retains the same biological activities. Furthermore, although the disease or disorder described above for the medical application of fragments of CMS-010 (VAPEEHPTLLTEAPLNPK) (wherein said fragments do not comprise the sequence of CMS-010) and functional derivatives thereof specifically recite cell proliferative and immunological disorders and/or diseases, these medical applications are used as non-limiting examples only and should not be used to limit the scope of the claims. It is clear that there are other possible/intended uses of fragments of CMS-010 (VAPEEHPTLLTEAPLNPK) (wherein said fragments do not comprise the sequence of CMS-010) and functional derivatives thereof, such as for use as a health food supplement to modulate the immune system of a normal person or a patient with any immune and/or cell proliferative disorders and/or diseases. Any such uses also fall within the scope of the present invention.

What is claimed is:

1. An isolated, purified peptide consisting of SEQ ID NO. 24.

2. A pharmaceutical composition, comprising a peptide and a pharmaceutically acceptable carrier; wherein the peptide consists of the isolated peptide of claim 1.

3. A method of treating nephritis, comprising administering to a subject in need thereof an effective amount of the peptide of claim 1.

4. The method according to claim 3, wherein the treatment of nephritis comprises decreasing the severity of proteinuria in nephritis.

5. A method of modulating the immune system, comprising administering to a subject in need thereof a therapeutically effective amount of a peptide of claim 1, wherein said modulation is selected from the group consisting of: suppressing transformation of T-lymphocytes, suppressing antibody formation and suppressing NK cell activity.

* * * * *

```
                        SEQUENCE LISTING

<160> NUMBER OF SEQ ID NOS: 31

<210> SEQ ID NO 1
<211> LENGTH: 18
<212> TYPE: PRT
<213> ORGANISM: Sus scrofa

<400> SEQUENCE: 1

Val Ala Pro Glu Glu His Pro Thr Leu Leu Thr Glu Ala Pro Leu Asn
1               5                   10                  15

Pro Lys

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 2

Ala Pro Glu Glu His Pro Thr Leu Leu Thr Glu Ala Pro Leu Asn Pro
1               5                   10                  15

Lys

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 3

Val Ala Pro Glu Glu His Pro Thr Leu Leu Thr Glu Ala Pro Leu Asn
1               5                   10                  15

Pro

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 4

Pro Glu Glu His Pro Thr Leu Leu Thr Glu Ala Pro Leu Asn Pro Lys
1               5                   10                  15
```

-continued

```
<210> SEQ ID NO 5
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 5

Val Ala Pro Glu Glu His Pro Thr Leu Leu Thr Glu Ala Pro Leu Asn
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 6

Val Ala Pro Glu Glu His Pro Thr Leu Leu Thr Glu Ala Pro Leu
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 7

Val Ala Pro Glu Glu His Pro Thr Leu Leu Thr Glu Ala Pro
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 8

Glu His Pro Thr Leu Leu Thr Glu Ala Pro Leu Asn Pro Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 9

His Pro Thr Leu Leu Thr Glu Ala Pro Leu Asn Pro Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 10

Val Ala Pro Glu Glu His Pro Thr Leu Leu Thr Glu
1               5                   10
```

```
<210> SEQ ID NO 11
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 11

Pro Thr Leu Leu Thr Glu Ala Pro Leu Asn Pro Lys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 12

Val Ala Pro Glu Glu His Pro Thr Leu Leu Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 13

Thr Leu Leu Thr Glu Ala Pro Leu Asn Pro Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 14

Val Ala Pro Glu Glu His Pro Thr Leu Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 15

Leu Leu Thr Glu Ala Pro Leu Asn Pro Lys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 16

Val Ala Pro Glu Glu His Pro Thr Leu
1               5
```

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 17

Leu Thr Glu Ala Pro Leu Asn Pro Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 18

Val Ala Pro Glu Glu His Pro Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 19

Thr Glu Ala Pro Leu Asn Pro Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 20

Val Ala Pro Glu Glu His Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 21

Glu Ala Pro Leu Asn Pro Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 22

Ala Pro Leu Asn Pro Lys
1               5

<210> SEQ ID NO 23

```
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 23

Val Ala Pro Glu Glu His
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 24

Pro Leu Asn Pro Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 25

Val Ala Pro Glu Glu
1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 26

Leu Asn Pro Lys
1

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 27

Val Ala Pro Glu
1

<210> SEQ ID NO 28
<211> LENGTH: 3
<212> TYPE: PRT
<213> ORGANISM: Artificial Sequence
<220> FEATURE:
<223> OTHER INFORMATION: Synthetic peptide sequence

<400> SEQUENCE: 28

Asn Pro Lys
1

<210> SEQ ID NO 29
<211> LENGTH: 2
```

-continued

```
<212> TYPE: PRT
<213> ORGANISM: Artificial
<220> FEATURE:
<223> OTHER INFORMATION: Synthetic peptide sequence

<400> SEQUENCE: 29

Val Ala
1

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 30

Val Ala Leu Leu Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 31

Val Ala Asn Pro Lys
1               5
```